US011751476B2

(12) United States Patent
Cho et al.

(10) Patent No.: US 11,751,476 B2
(45) Date of Patent: Sep. 5, 2023

(54) ELECTRON BUFFERING MATERIAL AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Sang-Hee Cho, Gyeonggi-do (KR); Jeong-Hwan Jeon, Gyeonggi-do (KR); Hong-Yeop Na, Gyeonggi-do (KR); Ji-Song Jun, Gyeonggi-do (KR); Jae-Hoon Shim, Gyeonggi-do (KR); Kyung-Hoon Choi, Gyeonggi-do (KR); Chi-Sik Kim, Gyeonggi-do (KR); Young-Jun Cho, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 46 days.

(21) Appl. No.: 17/328,729

(22) Filed: May 24, 2021

(65) Prior Publication Data

US 2021/0328155 A1    Oct. 21, 2021

Related U.S. Application Data

(63) Continuation of application No. 15/125,606, filed as application No. PCT/KR2015/002580 on Mar. 17, 2015, now abandoned.

(30) Foreign Application Priority Data

Mar. 17, 2014  (KR) ...................... 10-2014-0031264
Mar. 16, 2015  (KR) ........................ 10-2015-0036184

(51) Int. Cl.

| | | |
|---|---|---|
| H10K 85/60 | (2023.01) |
| C07D 403/14 | (2006.01) |
| C07D 409/14 | (2006.01) |
| C07D 487/04 | (2006.01) |
| C07D 495/04 | (2006.01) |
| C07D 403/12 | (2006.01) |
| C07D 405/14 | (2006.01) |
| C07D 405/04 | (2006.01) |
| C07D 471/04 | (2006.01) |
| C07D 403/04 | (2006.01) |
| H10K 85/30 | (2023.01) |
| C07D 403/10 | (2006.01) |
| C09K 11/02 | (2006.01) |
| C09K 11/06 | (2006.01) |
| H10K 30/80 | (2023.01) |

(Continued)

(52) U.S. Cl.
CPC ....... *H10K 85/6572* (2023.02); *C07D 403/04* (2013.01); *C07D 403/10* (2013.01); *C07D 403/12* (2013.01); *C07D 403/14* (2013.01); *C07D 405/04* (2013.01); *C07D 405/14* (2013.01); *C07D 409/14* (2013.01); *C07D 471/04* (2013.01); *C07D 487/04* (2013.01); *C07D 495/04* (2013.01); *C09K 11/025* (2013.01); *C09K 11/06* (2013.01); *H10K 85/30* (2023.02); *H10K 85/615* (2023.02); *H10K 85/626* (2023.02); *H10K 85/633* (2023.02); *H10K 85/654* (2023.02); *H10K 85/657* (2023.02); *H10K 85/6574* (2023.02); *H10K 85/6576* (2023.02); *C09K 2211/1007* (2013.01); *C09K 2211/1011* (2013.01); *C09K 2211/1014* (2013.01); *H10K 30/865* (2023.02); *H10K 50/157* (2023.02); *H10K 50/18* (2023.02)

(58) Field of Classification Search
CPC ............. H01L 51/0072; H01L 51/0052; H01L 51/0058; H01L 51/006; H01L 51/0067; H01L 51/0071; H01L 51/0073; H01L 51/0074; H01L 51/0077; H01L 51/5008; H01L 51/5068; H01L 51/5096; H01L 51/52; H01L 51/5024; C07D 403/04; C07D 403/10; C07D 403/12; C07D 403/14; C07D 405/04; C07D 405/14; C07D 409/14; C07D 471/04; C07D 487/04; C07D 495/04; C09K 11/025; C09K 11/06; C09K 2211/1007; C09K 2211/1011; C09K 2211/1014; H10K 85/6572; H10K 85/30; H10K 85/615; H10K 85/626; H10K 85/633; H10K 85/654; H10K 85/657; H10K 85/6574; H10K 85/6576; H10K 30/865; H10K 50/157; H10K 50/18; H10K 50/80; H10K 50/12

See application file for complete search history.

(56) References Cited

U.S. PATENT DOCUMENTS

| | | | | |
|---|---|---|---|---|
| 2010/0045175 A1* | 2/2010 | Mathai | .................... | H01L 51/52 |
| | | | | 257/E51.026 |
| 2012/0056165 A1* | 3/2012 | Kawamura | ......... | H01L 51/0052 |
| | | | | 252/301.16 |
| 2013/0292664 A1* | 11/2013 | Nishimura | .............. | C09B 57/10 |
| | | | | 257/40 |

FOREIGN PATENT DOCUMENTS

WO   WO-2014014310 A1 *  1/2014  ........... C07D 209/86

OTHER PUBLICATIONS

Liu et al., (2012), Physical Chemistry Chemical Physics, 14(41), 14255-14261. (Year: 2012).*

(Continued)

*Primary Examiner* — Dawn L Garrett
(74) *Attorney, Agent, or Firm* — G. Creston Campbell

(57) ABSTRACT

The present invention relates to an electron buffering material and an organic electroluminescent device comprising the same in an electron buffer layer. It is possible to provide an organic electroluminescent device having excellent lumi- (Continued)

nous efficiency and lifespan characteristics by using the electron buffering material according to the present invention.

7 Claims, 2 Drawing Sheets

(51) Int. Cl.
    *H10K 50/18*     (2023.01)
    *H10K 50/15*     (2023.01)

(56) References Cited

OTHER PUBLICATIONS

Hudson, Z. M., Wang, Z., Helander, M. G., Lu, Z. H., & Wang, S. (2012). N-Heterocyclic Carbazole-Based Hosts for Simplified Single-Layer Phosphorescent OLEDs with High Efficiencies. Advanced Materials, 24(21), 2922-2928. (Year: 2012).*

* cited by examiner

ELECTRON BUFFERING MATERIAL AND ORGANIC ELECTROLUMINESCENT DEVICE COMPRISING THE SAME

CLAIM OF BENEFIT OF PRIOR APPLICATION

This application claims priority under 35 U.S.C. § 120 from U.S. patent application Ser. No. 15/125,606, filed Sep. 13, 2016, which is the National Stage Entry of PCT/KR2015/002580, filed Mar. 17, 2015, both of which are incorporated by reference herein in their entirety.

TECHNICAL FIELD

The present invention relates to an electron buffering material and an organic electroluminescent device comprising the same.

BACKGROUND ART

After Tang et al. of Eastman Kodak first developed a TPD/Alq3 bilayer small molecule green organic electroluminescent device (OLED) composed of a light-emitting layer and an electron transport layer in 1987, studies of organic electroluminescent devices have been rapidly conducted, and now became commercialized. At present, phosphorescent materials, which have excellent luminous efficiency, are mainly used for panels of the organic electroluminescent devices. In the case of red and green light-emitting organic electroluminescent devices, commercialization of organic electroluminescent devices using phosphorescent materials succeeded, but in the case of blue phosphorescent materials, characteristics deteriorate due to decrease of roll-off at high current by loss of excessively formed excitons, the blue phosphorescent material itself reveals problems in long-term lifespan stability, and the color purity sharply drops as time passes, thus realization of full color display is disrupted.

The blue fluorescent materials used at present also have several problems. First, when exposed to high temperature during a process of producing a panel, a current characteristic of the blue fluorescent luminescent device changes to cause a problem of a change in luminance, and a drop of an interfacial characteristic between a light-emitting layer and an electron injection layer causes a decrease in luminance. Second, in the case of devices comprising an anthracene based blue fluorescent host and a pyrene based dopant, an absolute value of a LUMO (lowest unoccupied molecular orbital) energy of the host (Ah) is higher than that of the dopant (Ad), and hole traps are magnified so that efficiency increases due to interfacial luminescence between the electron transport layer and the fluorescent light-emitting layer, but there is a problem in that the lifespan decreases.

In Applied Physics Letters 90, 123506 (2007), a blue fluorescent light-emitting device comprising an electron buffer layer is realized. However, the reference only focuses on a coordinate shift by doping an amine-based dopant to an anthracene-based host, and a control of a light-emitting zone and color coordinate enhancement by the electron buffer layer, and an increase in luminous efficiency or improvement in lifespan by inserting an electron buffer layer are not disclosed.

Japanese patent no. 4947909 discloses a blue fluorescent light-emitting device comprising an electron buffer layer, electrons which are efficiently injected to the light-emitting layer compared to Alq3 by inserting the electron buffer layer, and that mobility is varied to lower the driving voltage and enhance lifespan by preventing degradation of the light-emitting interface. However, the electron buffering materials are limited to Alq3 derivatives, the group of the materials is small, and thus analysis of effective luminous efficiency and lifespan improvement is limited.

DISCLOSURE OF THE INVENTION

Problems to be Solved

The objective of the present invention is to provide an electron buffer layer which can produce an organic electroluminescent device having excellent luminous efficiency and lifespan characteristics, and an organic electroluminescent device comprising the same.

Solution to Problems

The present inventors found that the above objective can be achieved by an electron buffering material comprising a compound comprising a nitrogen-containing heteroaryl.

Effects of the Invention

By using the electron buffering material according to the present invention, an electron injection is controlled, and the interfacial characteristic between the light-emitting layer and the electron injection layer is improved, and so it is possible to manufacture an organic electroluminescent device having excellent luminous efficiency and lifespan characteristics.

EMBODIMENTS OF THE INVENTION

Figure 1:
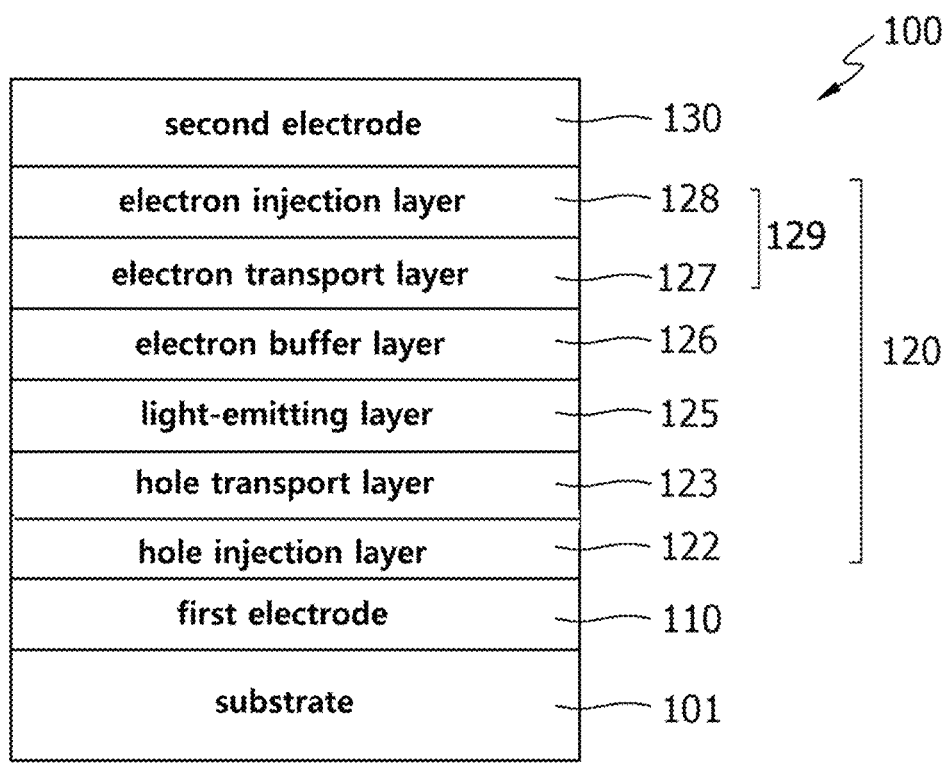
FIG. 1 illustrates a schematic sectional view of an organic electroluminescent device comprising the electron buffering material according to one embodiment of the present invention.

Hereinafter, the present invention will be described in detail. However, the following description is intended to explain the invention, and is not meant in any way to restrict the scope of the invention.

The present invention relates to an electron buffering material comprising a compound comprising a nitrogen-containing heteroaryl, and an organic electroluminescent device comprising a first electrode; a second electrode facing the first electrode; a light-emitting layer between the first electrode and the second electrode; and an electron transport zone and an electron buffer layer between the light-emitting layer and the second electrode, wherein the electron buffer layer comprises the compound comprising a nitrogen-containing heteroaryl.

The electron buffering material according to the present invention can be a mixture or composition additionally comprising a material commonly used when producing an organic electroluminescent device.

In an organic electroluminescent device comprising first and second electrodes, and a light-emitting layer, an electron buffer layer can be inserted between the light-emitting layer and the second electrode to focus on obtaining high efficiency due to electron injection controlled by the LUMO energy level of the electron buffer layer and long lifespan.

Originally, LUMO (lowest unoccupied molecular orbital) energy and HOMO (highest occupied molecular orbital) energy levels have negative values. However, for convenience LUMO energy level (A) and HOMO energy level are expressed in absolute values in the present invention. In addition, the values of the LUMO energy level are compared based on absolute values.

The electron buffer layer and the electron transport zone are inserted between the light-emitting layer and the second electrode. The electron buffer layer can be located between the light-emitting layer and the electron transport zone, or between the electron transport zone and the second electrode.

In the present invention, an electron transport zone means a zone in which electrons are transported from the second electrode to the light-emitting layer. The electron transport zone can comprise an electron transport compound, a reductive dopant, or a combination thereof. The electron transport compound can be at least one selected from a group comprising oxazole-based compounds, isoxazole-based compounds, triazole-based compounds, isothiazole-based compounds, oxadiazole-based compounds, thiadiazole-based compounds, perylene-based compounds, anthracene-based compounds, aluminum complexes, and gallium complexes. The reductive dopant can be at least one selected from a group consisting of alkali metals, alkali metal compounds, alkaline-earth metals, rare earth metals, halides thereof, oxides thereof, and complexes thereof. In addition, the electron transport zone can comprise an electron transport layer, an electron injection layer, or both of them. The electron transport layer and the electron injection layer can each be composed of two or more layers.

FIG. 1 illustrates a schematic sectional view of an organic electroluminescent device comprising the electron buffering material according to one embodiment of the present invention.

By inserting the electron buffer layer in the organic electroluminescent device, injection and transport of electrons can be controlled due to the difference of affinities between the light-emitting layer and the electron transport zone in accordance with LUMO energy levels.

Figure 2:
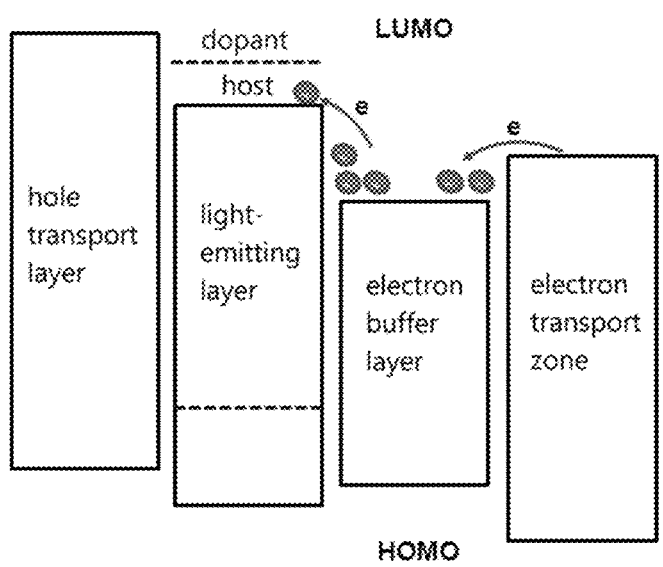
FIG. 2 illustrates an energy gap relationship among the layers of the organic electroluminescent device according to one embodiment of the present invention.

FIG. 2 illustrates an energy gap relationship among the layers of the organic electroluminescent device according to one embodiment of the present invention.

Figure 3:
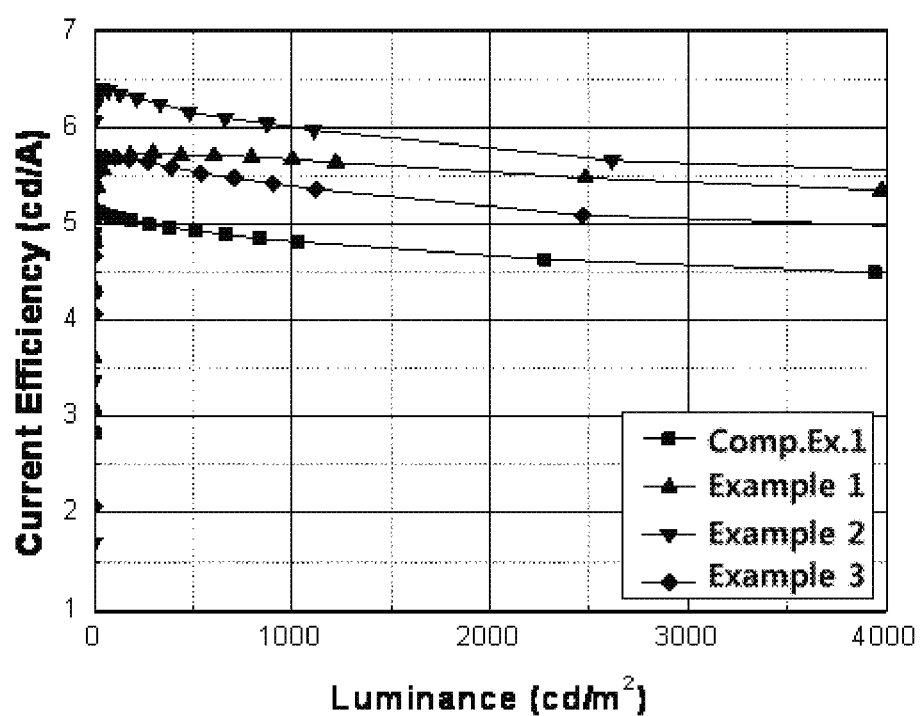
FIG. 3 illustrates a comparison of luminous efficiency between an organic electroluminescent device comprising an electron buffer layer and an organic electroluminescent device not comprising any electron buffer layer.

A comparison between when an electron buffer layer is comprised and when an electron buffer layer is not comprised is illustrated in FIG. 3. An organic electroluminescent device in which an electron buffer layer is inserted has higher current efficiency. The above will be described in detail hereinafter.

In the electron buffer layer of the present invention, a nitrogen-containing heteroaryl can be a triazine derivative, a pyrimidine derivative, a quinazoline derivative, a quinoxaline derivative, etc. Electron injection characteristics can be controlled by varying the nitrogen-containing heteroaryl.

An electron buffering material compound comprising a triazine derivative can obtain suitable efficiency and lifespan characteristic through a specific level of restraint of electron injection by taking advantage of an appropriate barrier against the light-emitting layer.

An electron buffering material compound comprising a pyrimidine derivative can contribute to efficiency increase of the device by minimizing the electron injection barrier from the light-emitting layer in accordance with low LUMO energy levels.

An electron buffering material compound comprising a quinazoline or quinoxaline shows a big improvement of lifespan rather than the efficiency of the device by excessive electron injection block in accordance with high LUMO energy levels.

The compound comprising a nitrogen-containing heteroaryl comprised in the electron buffering material can be selected from the compounds represented by the following formulae 1 to 3:

(1)

(2)

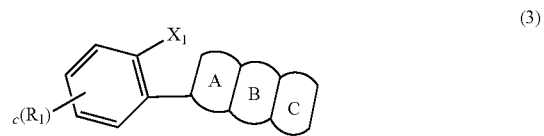

(3)

wherein

Cz represents the following structure:

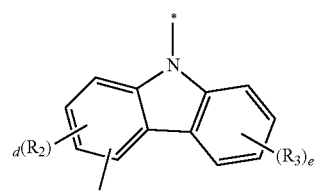

A represents

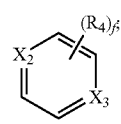

B represents

C represents

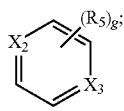

$R_1$ to $R_5$ each independently represent hydrogen, deuterium, a halogen, a substituted or unsubstituted (C1-C30) alkyl, a substituted or unsubstituted (C6-C30)aryl, a substituted or unsubstituted (5- to 30-membered)heteroaryl, or —$SiR_6R_7R_8$; or $R_1$ to $R_5$ each independently are linked to an adjacent substituent(s) to form a mono- or polycyclic, substituted or unsubstituted (C3-C30) alicyclic or aromatic ring, whose carbon atom(s) may be replaced with at least one hetero atom selected from nitrogen, oxygen, and sulfur;

$R_6$ to $R_8$ each independently represent a substituted or unsubstituted (C1-C30)alkyl, or a substituted or unsubstituted (C6-C30)aryl;

$L_1$ represents a single bond, a substituted or unsubstituted (C6-C30)arylene, or a substituted or unsubstituted (5- to 30-membered)heteroarylene;

M represents a substituted or unsubstituted (C6-C30)aryl, or a substituted or unsubstituted (5- to 30-membered)heteroaryl;

Cz, $L_1$, and M may be fused to an adjacent substituent(s) to form a ring;

$X_1$ to $X_3$ each independently represent —$N(R_9)$— or —$C(R_{10})(R_{11})$—;

Y represents —O—, —S—, —$C(R_{12})(R_{13})$—, —$Si(R_{14})(R_{15})$—, or —$N(R_{16})$—;

$R_9$ to $R_{16}$ each independently represent hydrogen, deuterium, a halogen, a substituted or unsubstituted (C1-C30) alkyl, a substituted or unsubstituted (C6-C30)aryl, a substituted or unsubstituted (5- to 30-membered)heteroaryl, a substituted or unsubstituted (5- to 7-membered)heterocycloalkyl, or a (5- to 7-membered)heterocycloalkyl fused with at least one substituted or unsubstituted aromatic ring, and $R_9$ to $R_{16}$ may be the same or different; and $R_{10}$ and $R_{11}$ may be linked to each other to form a mono- or polycyclic, substituted or unsubstituted (C3-C30) alicyclic or aromatic ring, whose carbon atom(s) may be replaced with at least one hetero atom selected from nitrogen, oxygen, and sulfur;

a, b, and d each independently represent an integer of 1 to 3;

c, e, and g each independently represent an integer of 1 to 4;

f represents 1 or 2; and where a, b, c, d, e, f, or g is an integer of 2 or more, each of (Cz-$L_1$), each of (Cz), each of $R_1$, each of $R_2$, each of $R_3$, each of $R_4$, or each of $R_5$ may be the same or different.

The specific compounds of which the nitrogen-containing heteroaryl is triazine include the following compounds, but are not limited thereto:

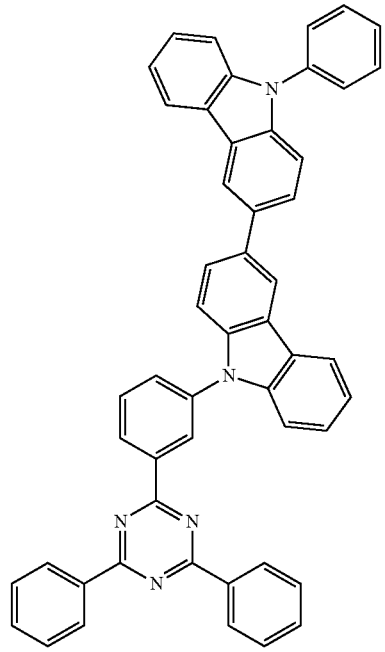

C-1

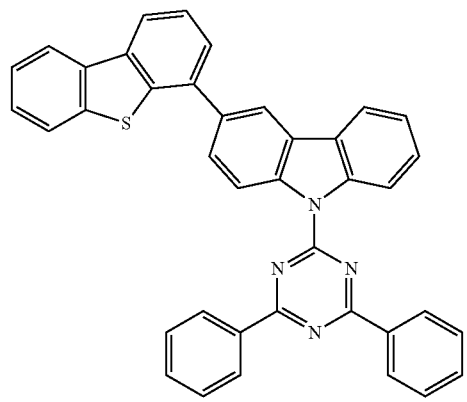

C-2

C-3
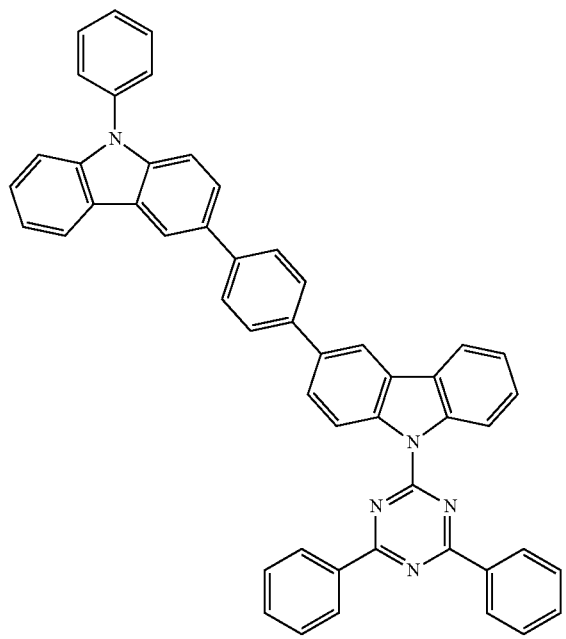
C-4
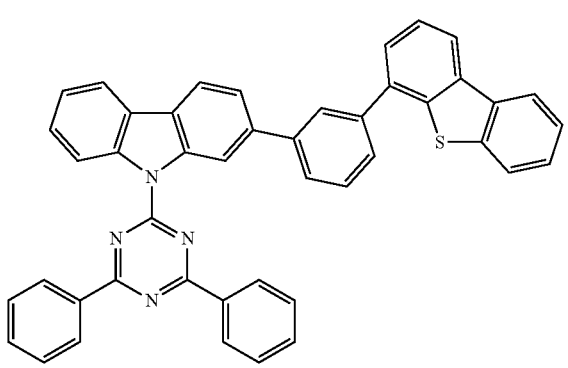
C-5
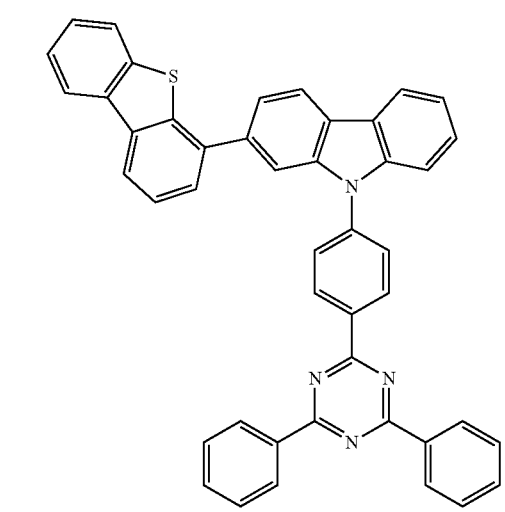
C-6
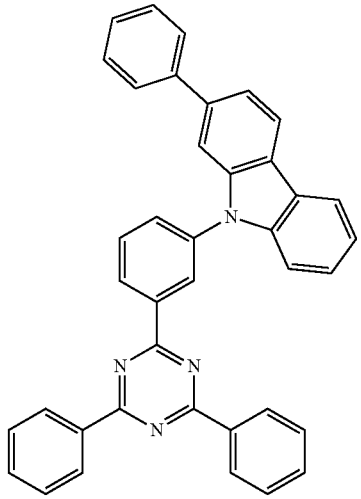
C-7
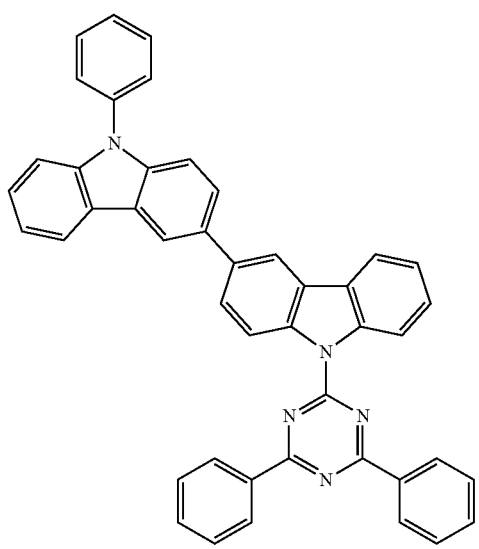
C-8
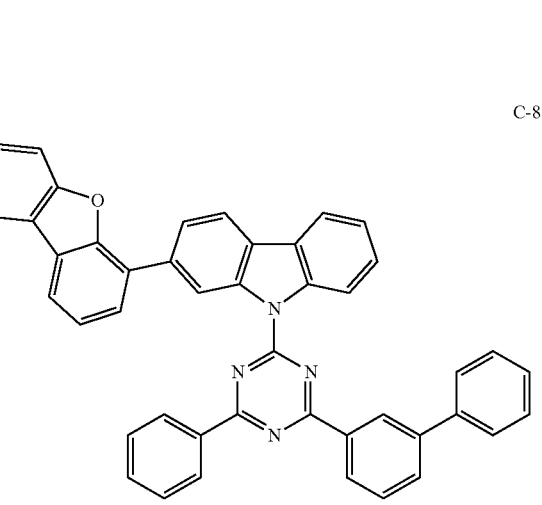

-continued
C-9
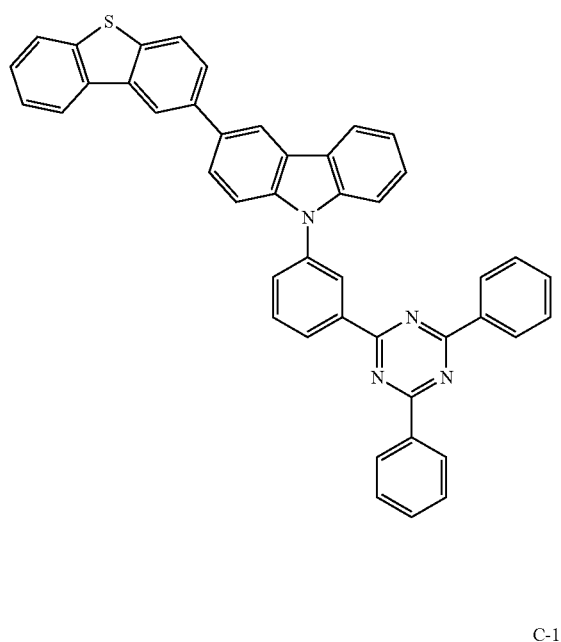
C-10
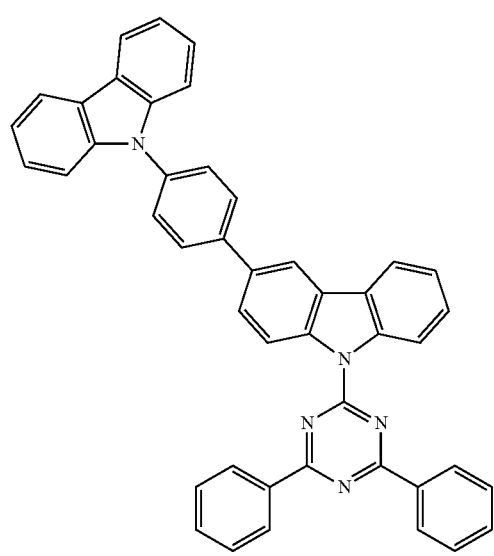
C-11
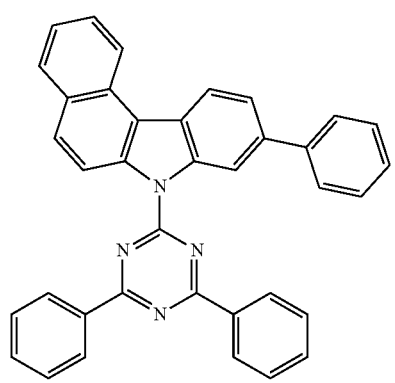
-continued
C-12
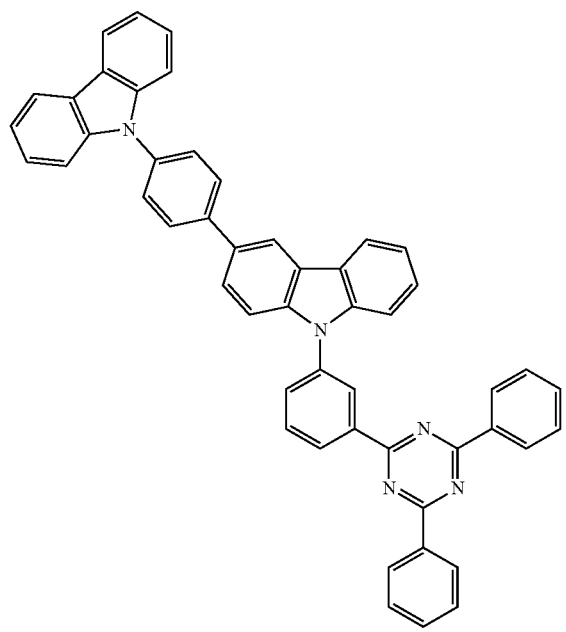
C-13
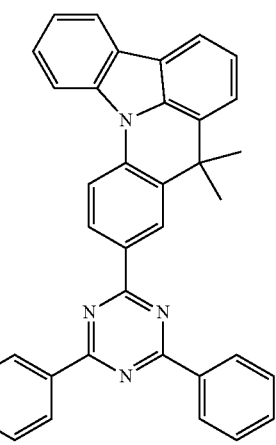
C-14

C-15
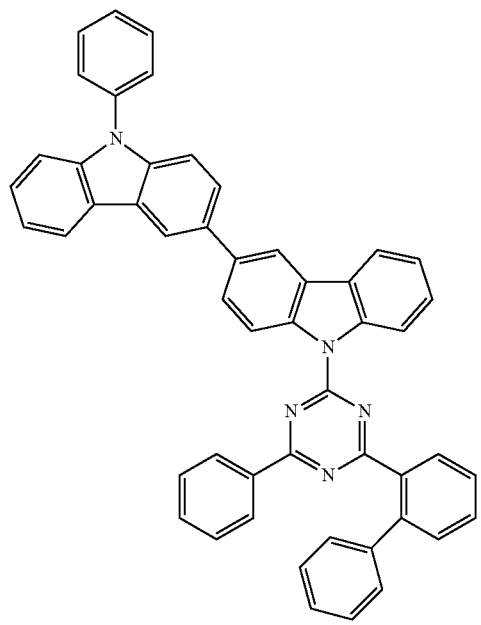
C-16
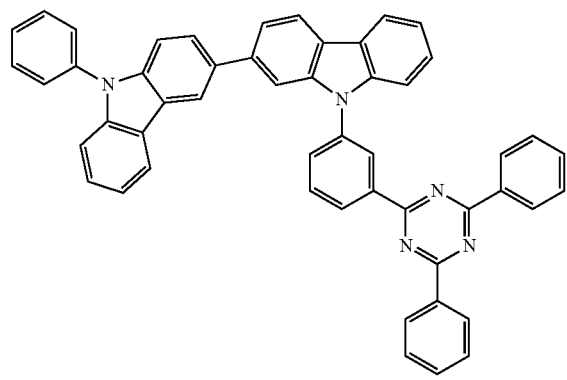
C-17
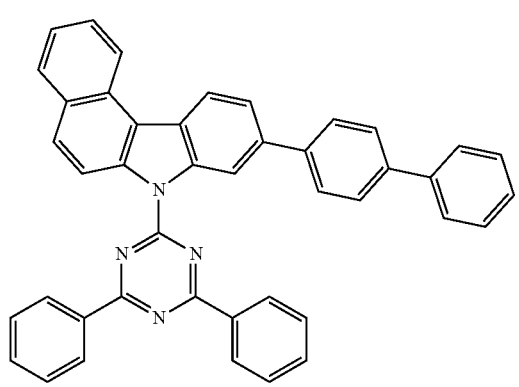
C-18
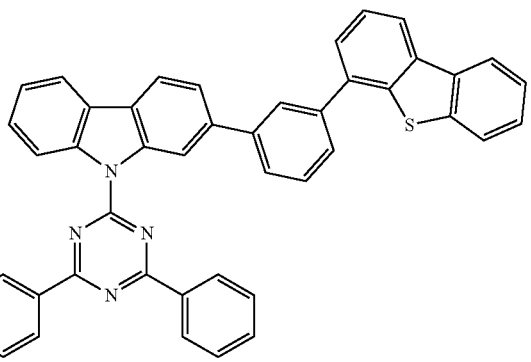
C-19
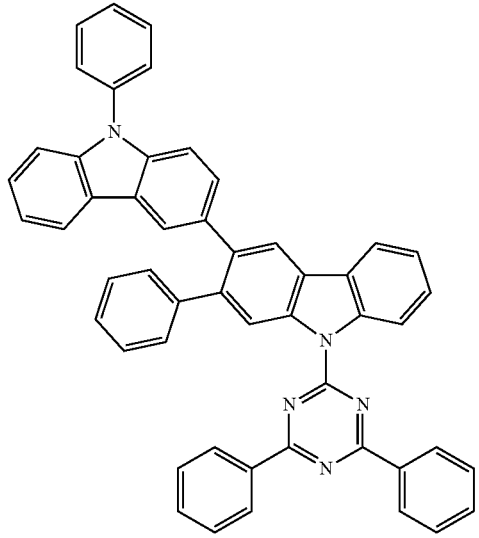
C-20
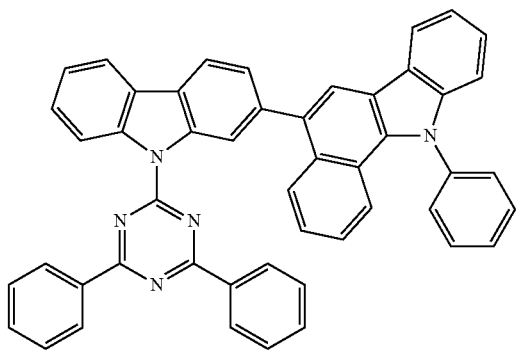

-continued
C-21
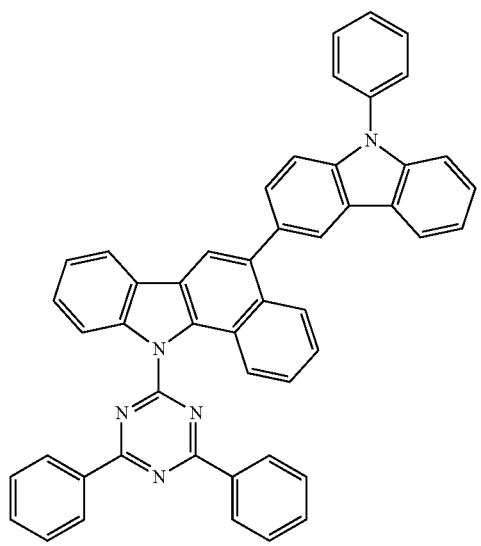
C-22
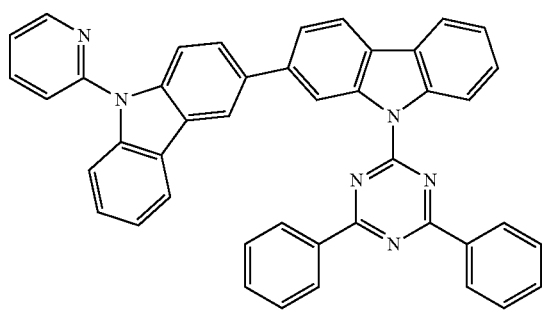
C-23
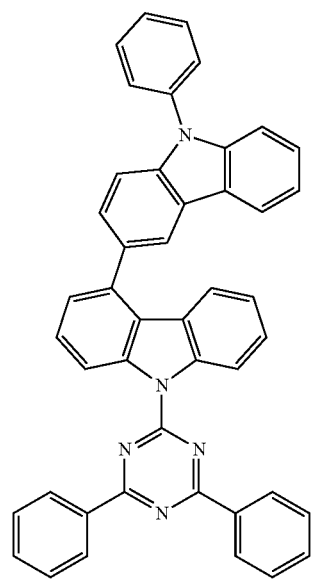
C-24
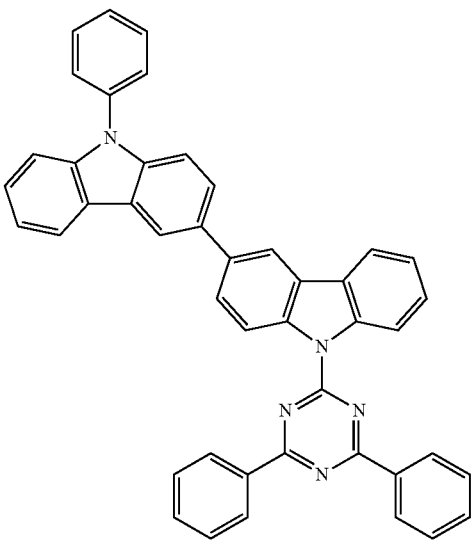
C-25
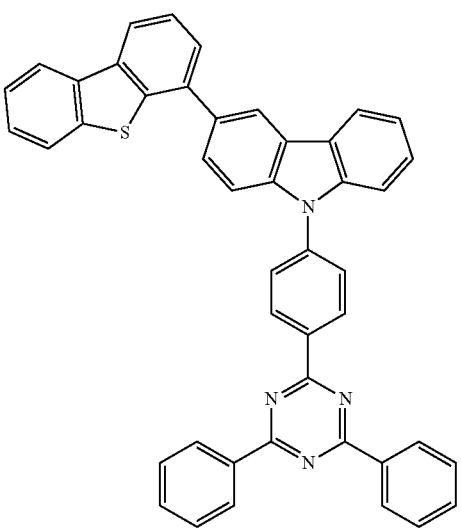
C-26
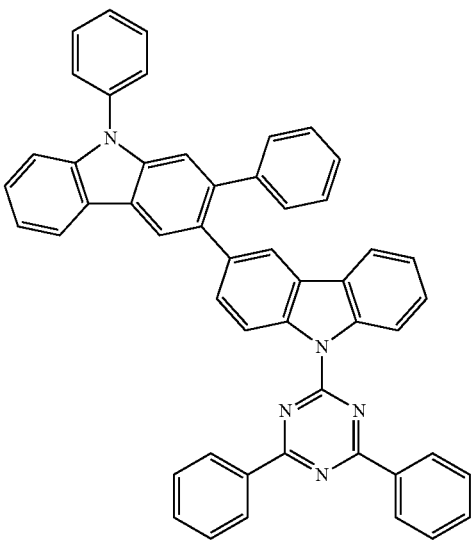

C-27
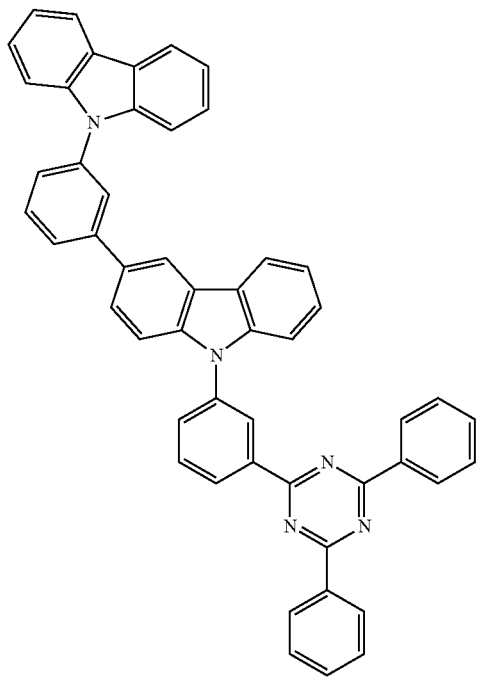
C-28
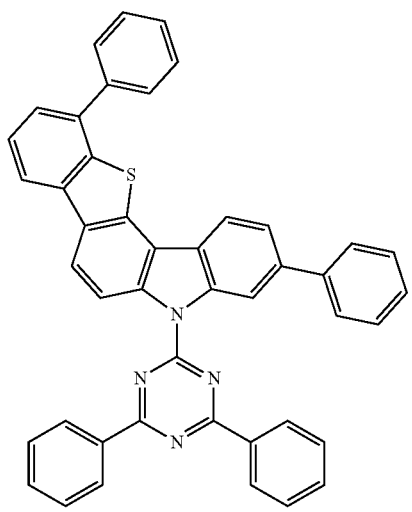
C-29
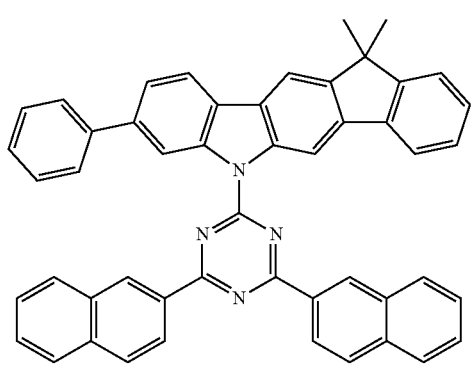
C-30
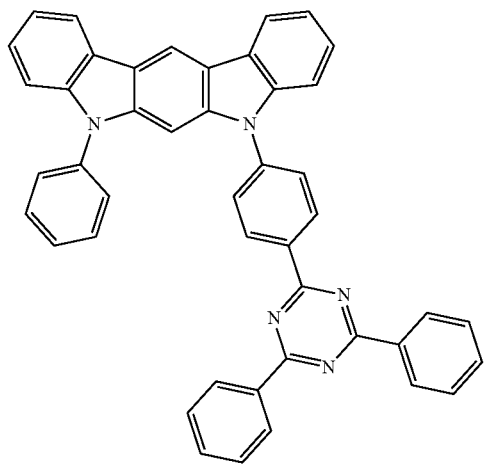
C-31
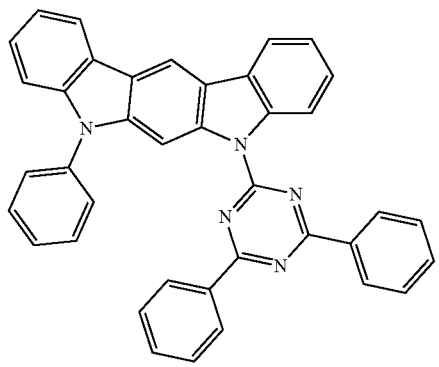
C-32
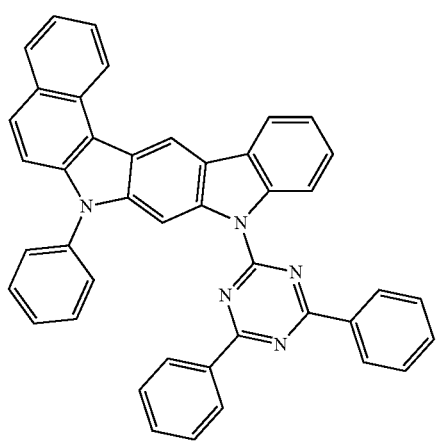

C-33
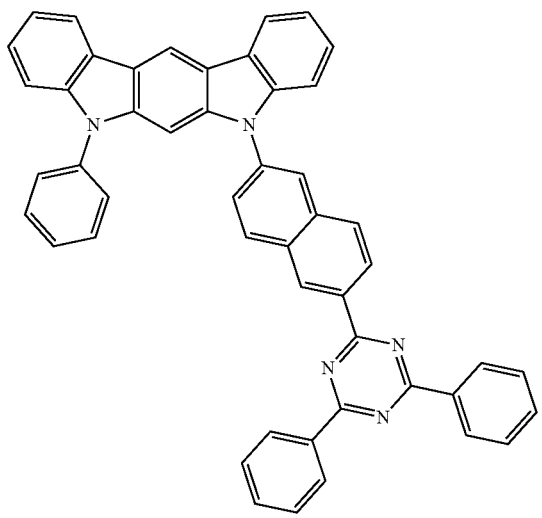
C-34
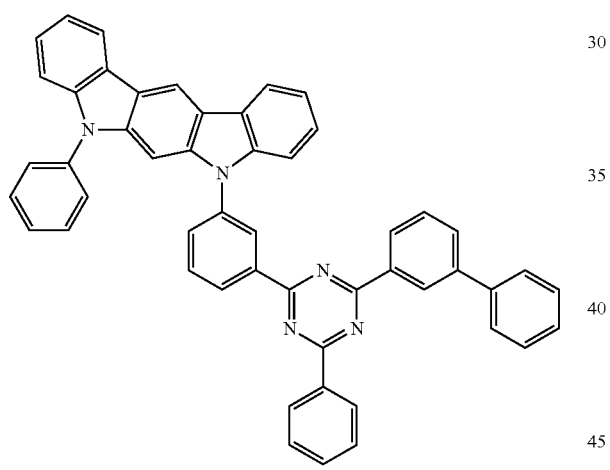
C-35
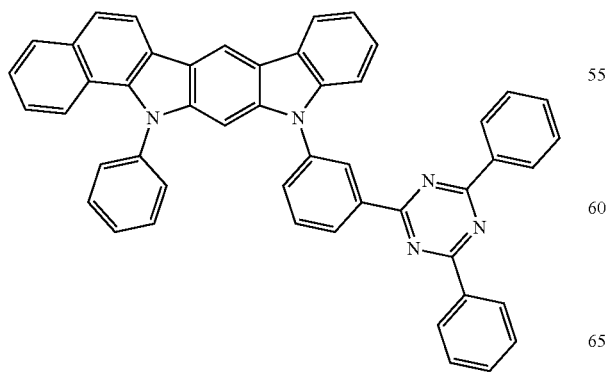
C-36
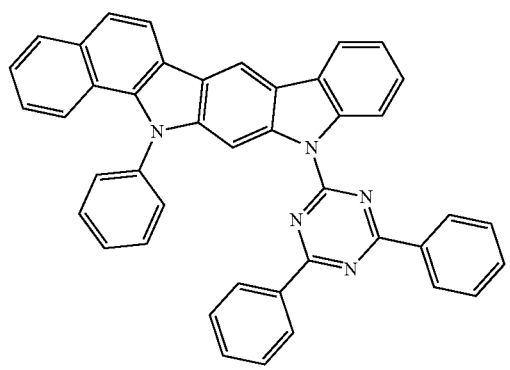
C-37
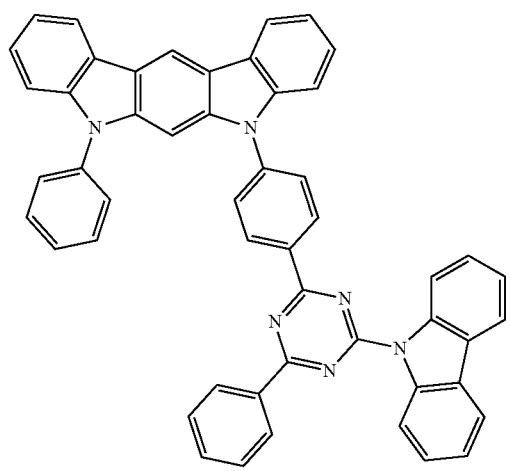
C-38
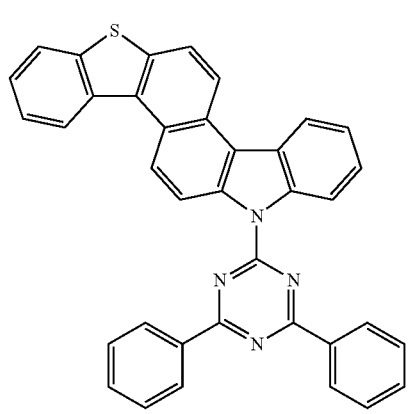

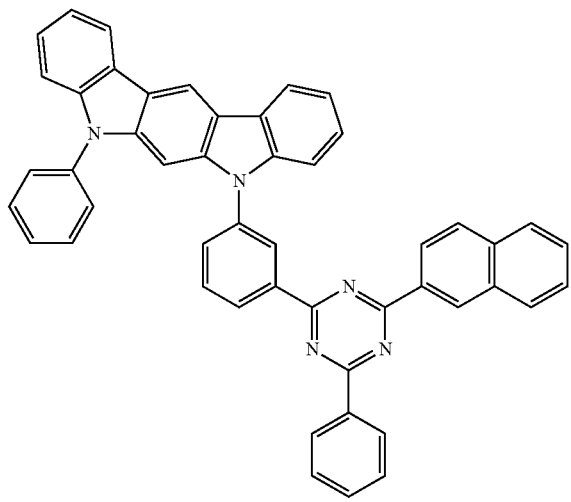
C-39
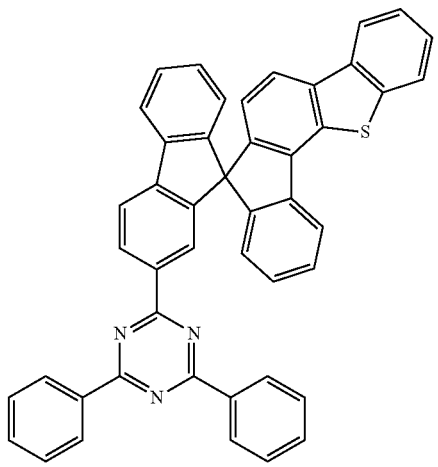
C-42
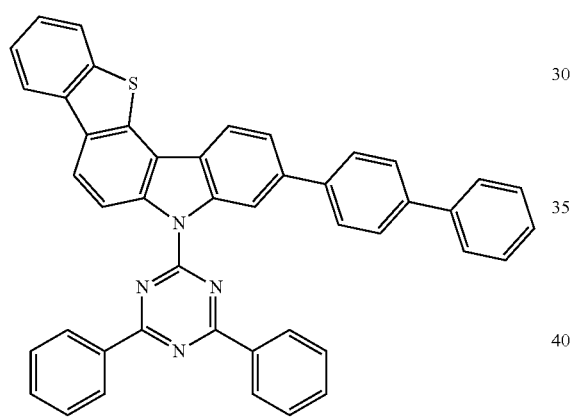
C-40
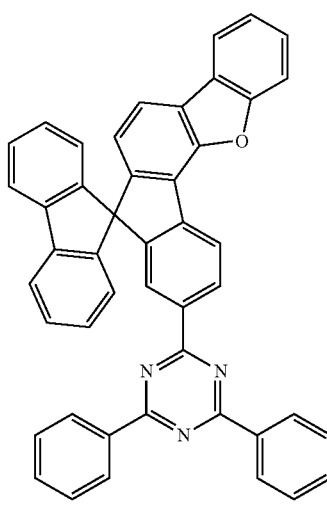
C-43
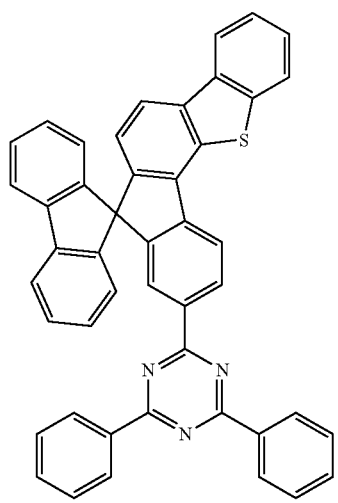
C-41
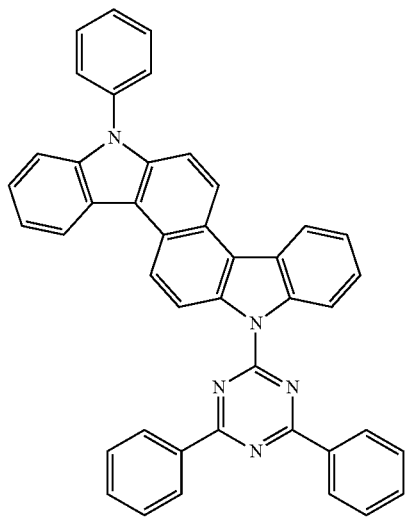
C-44

C-45
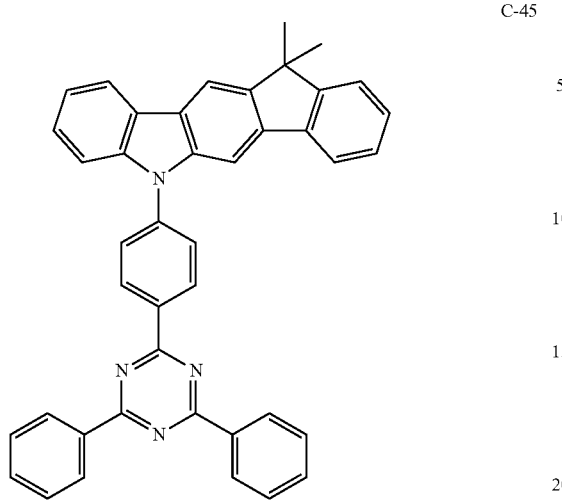
C-48
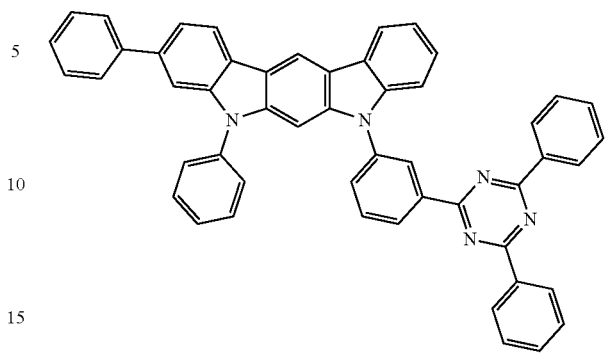
C-46
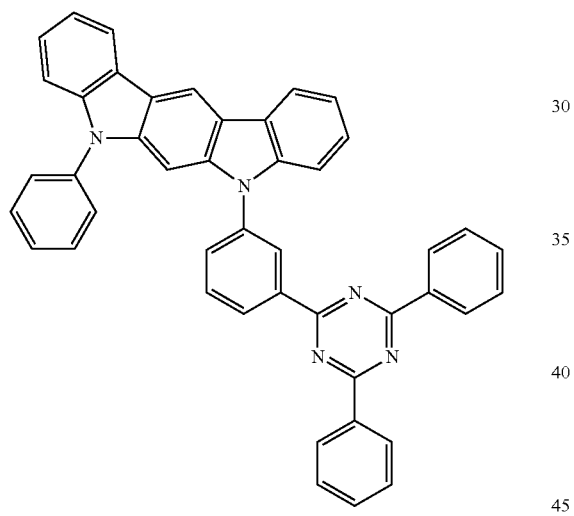
C-49
C-47
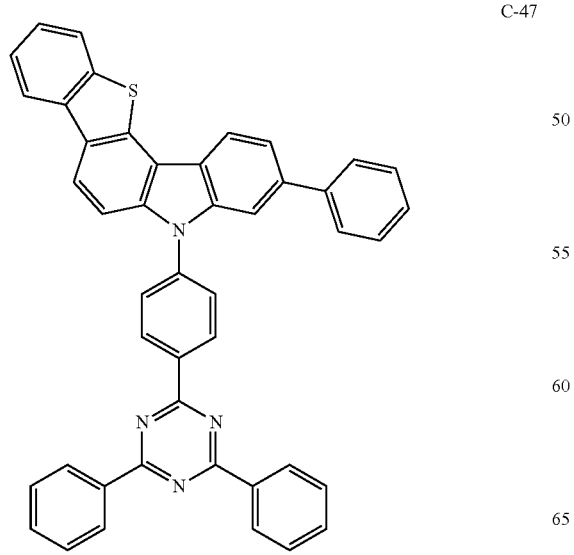
C-50

C-51
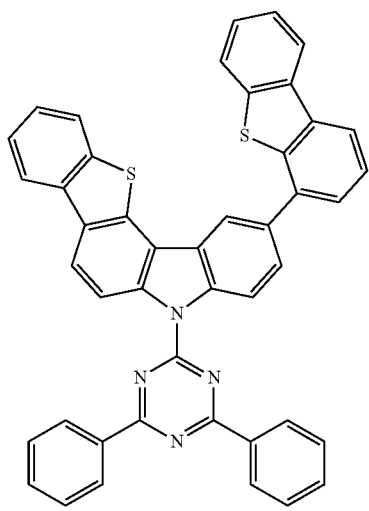
C-52
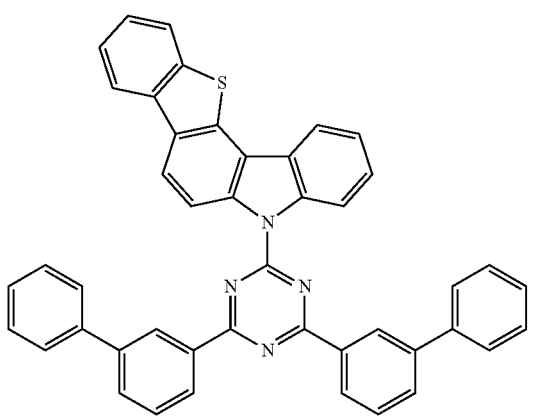
C-53
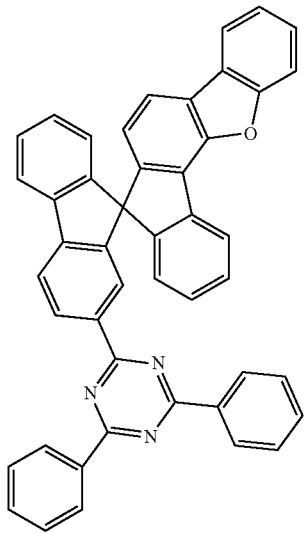
The specific compounds of which the nitrogen-containing heteroaryl is pyrimidine include the following compounds, but are not limited thereto:
C54
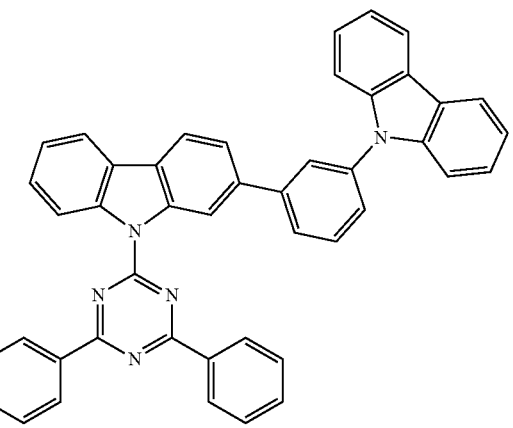
C-55
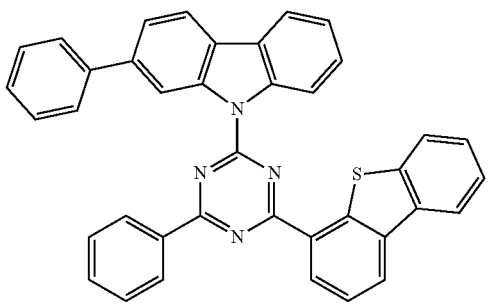
C-56
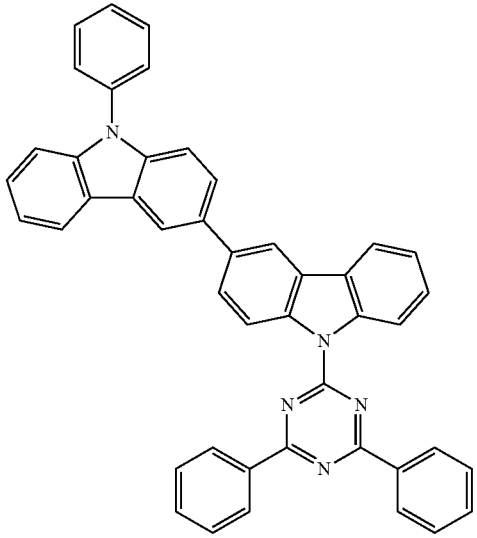

C-57
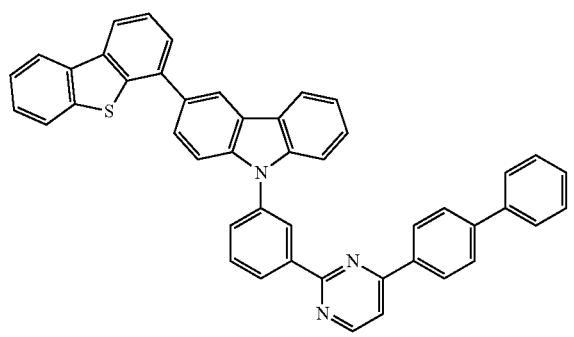
C-58
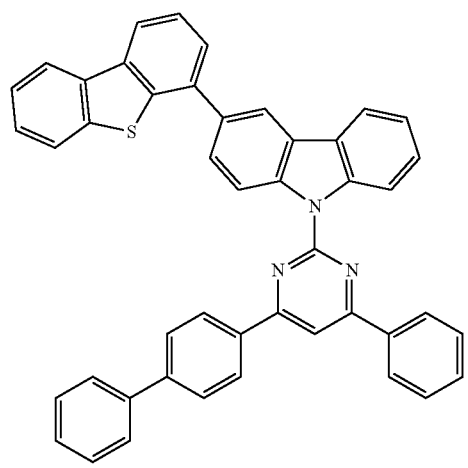
C-59
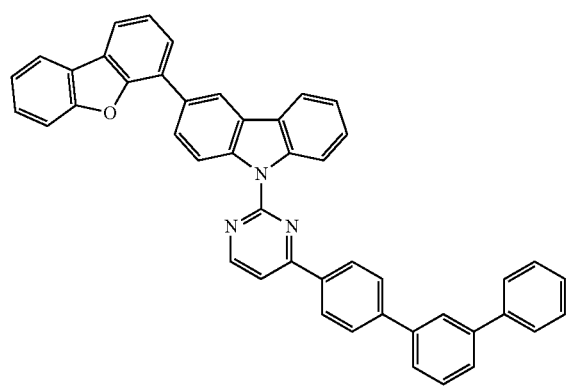
C-60
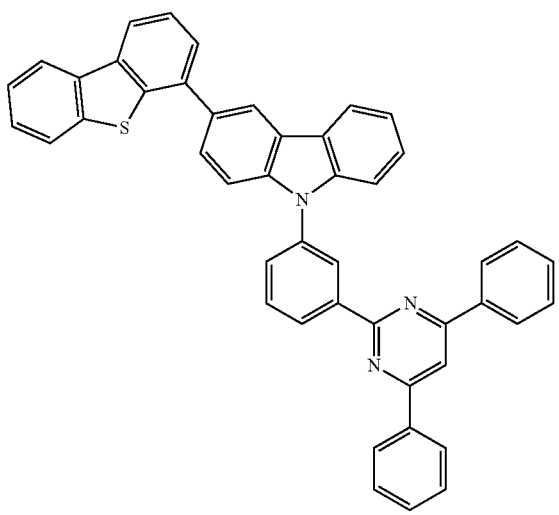
C-61
C-62
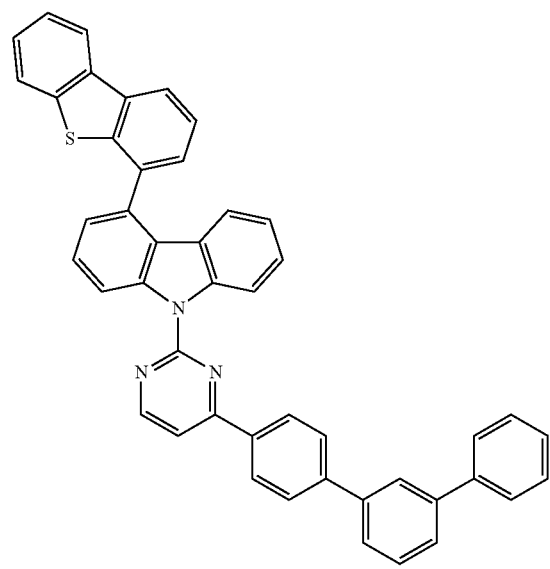

-continued
C-63
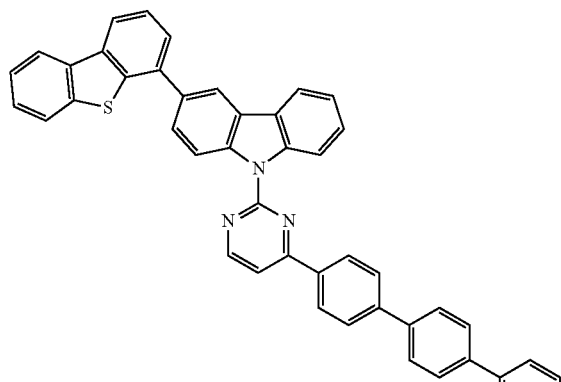
C-64
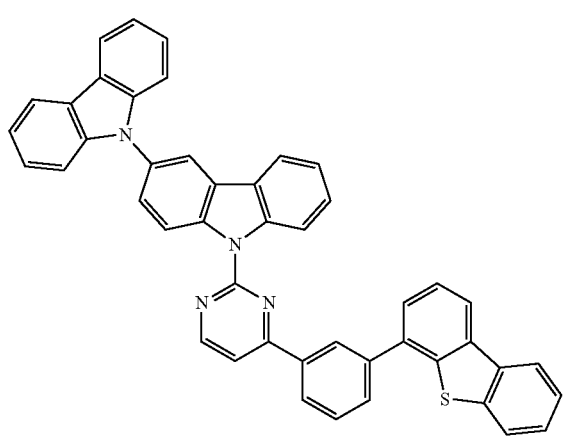
C-65
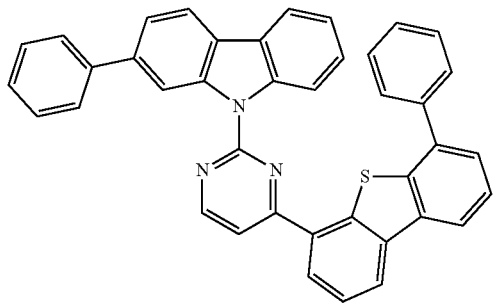
C-66
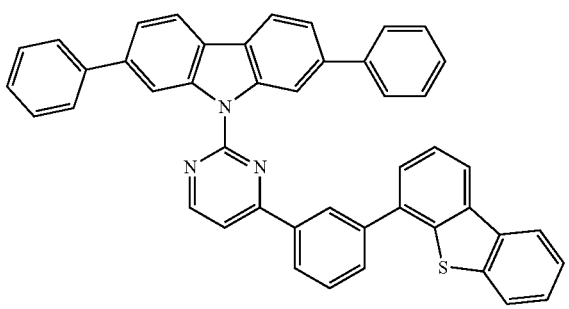
-continued
C-67
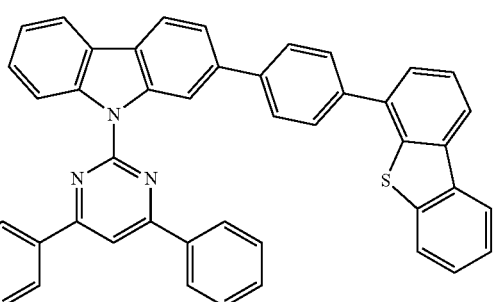
C-68
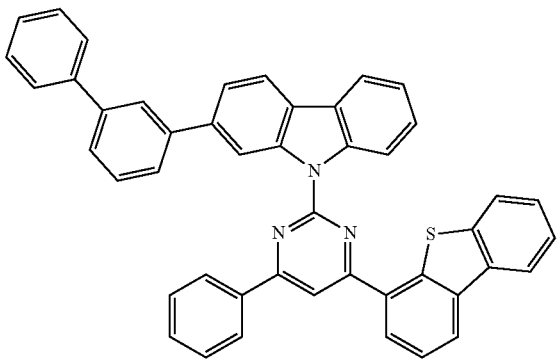
C-69
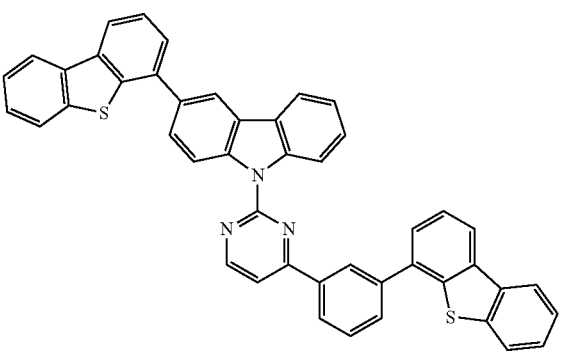
C-70
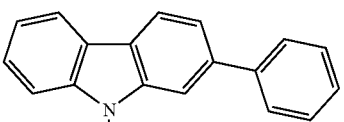
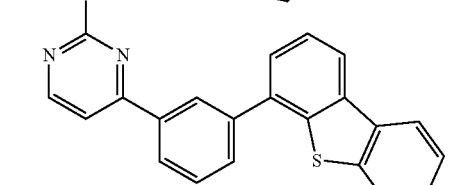

C-71
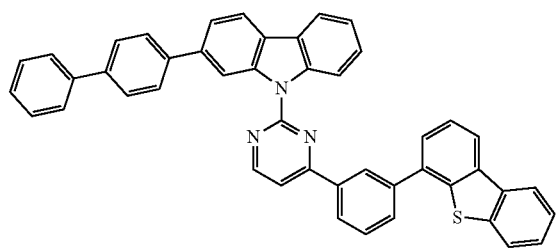
C-72
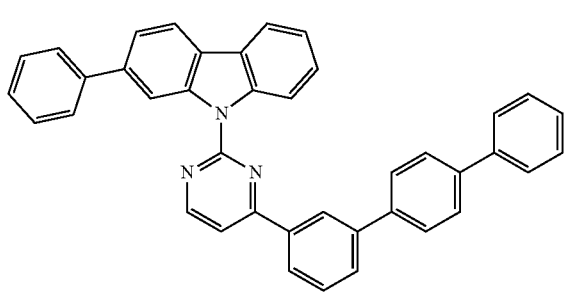
C-73
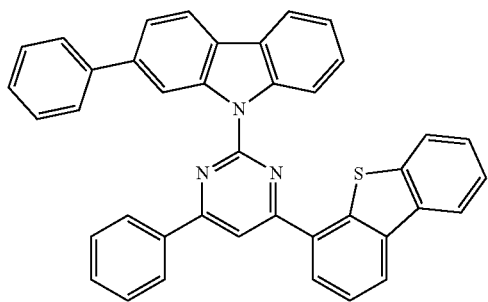
C-74
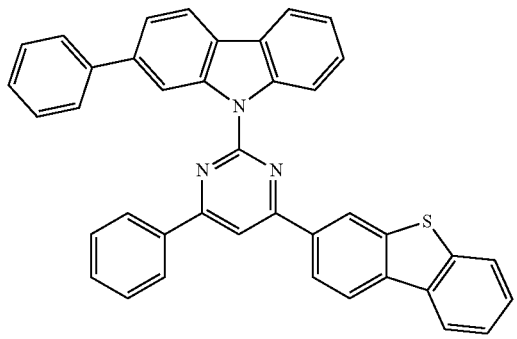
C-75
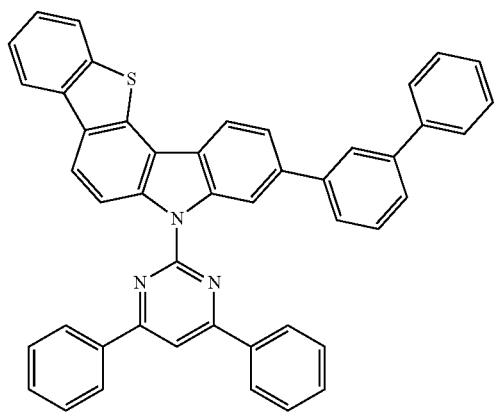
C-76
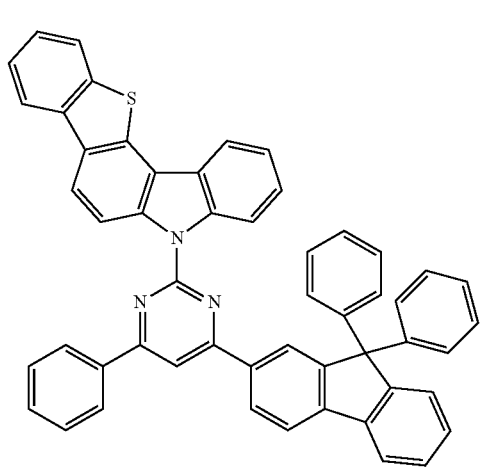
C-77
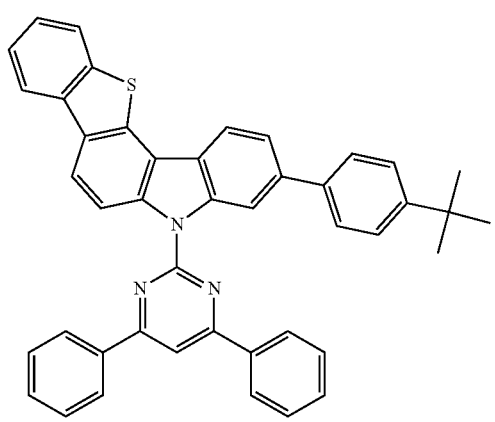

C-78
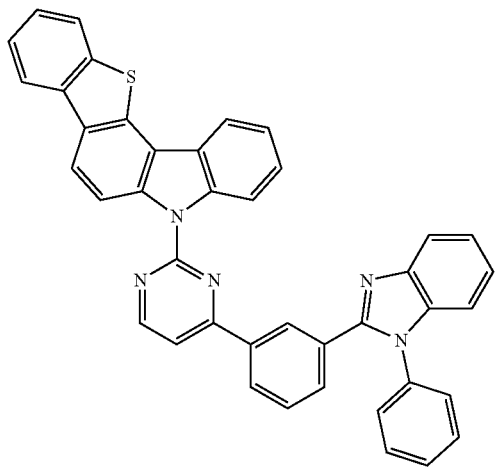
C-79
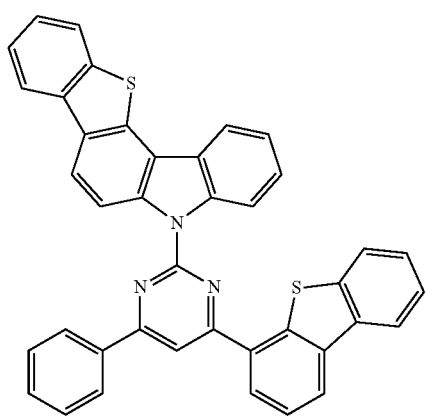
C-80
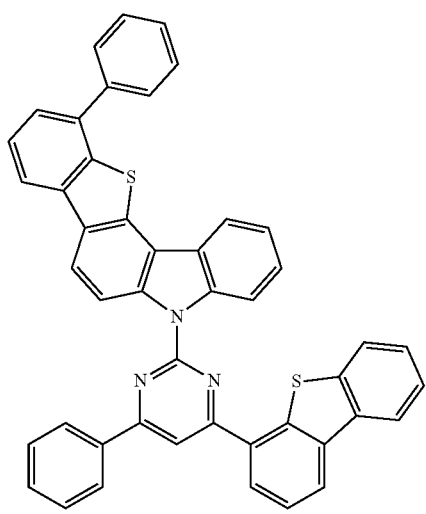
C-81
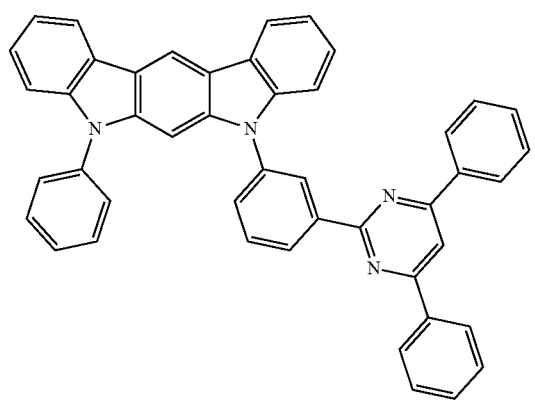
C-82
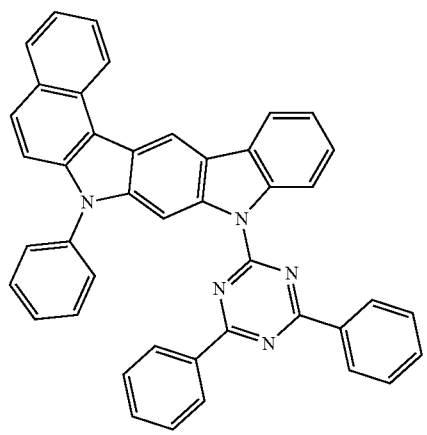
C-83
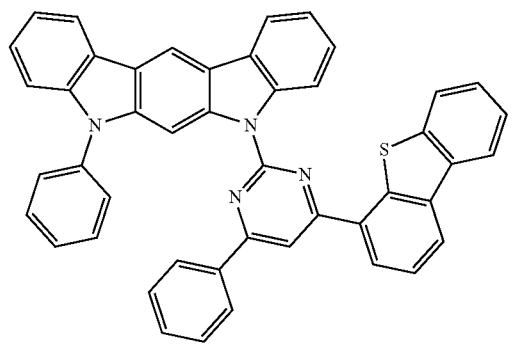

C-84
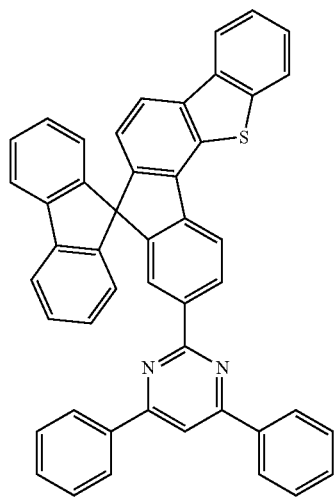
C-87
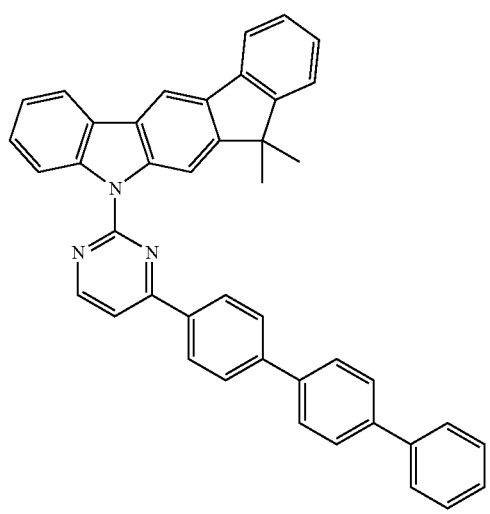
C-85
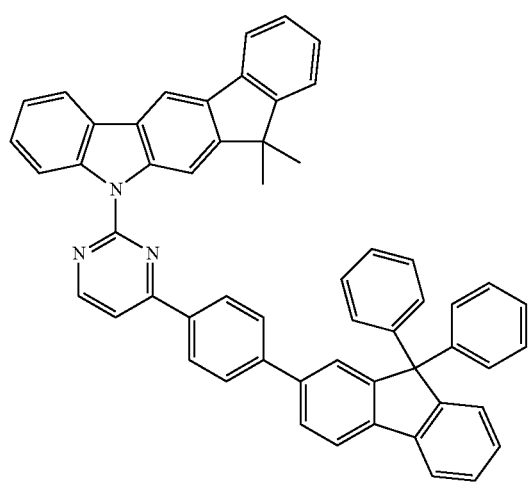
C-88
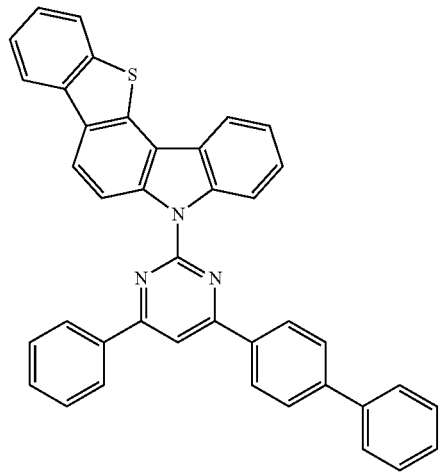
C-86
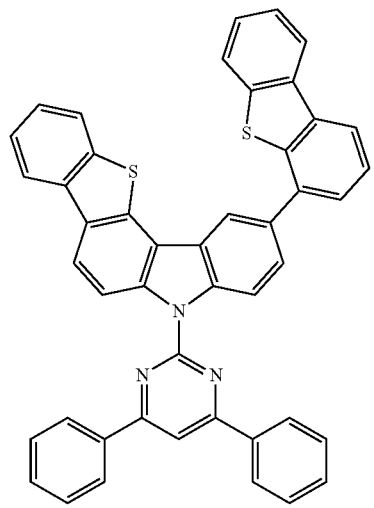
C-89
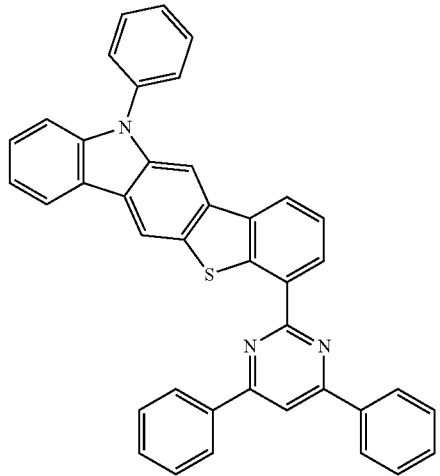

-continued
C-90
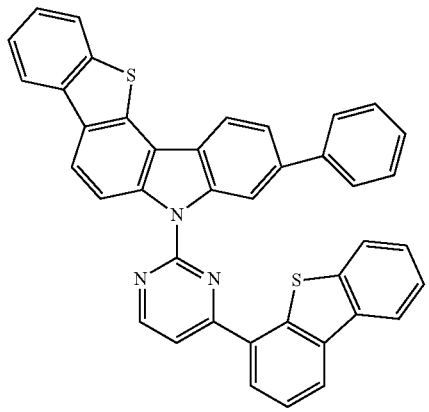
C-91
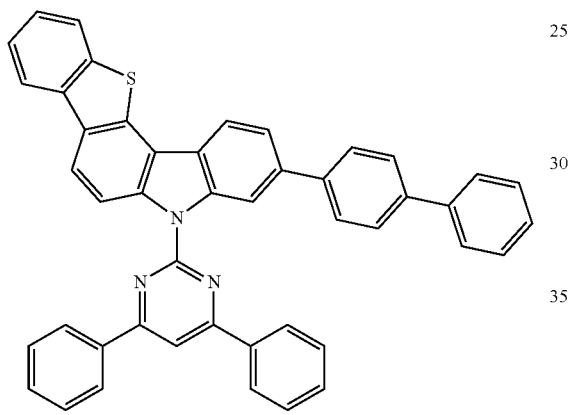
C-92
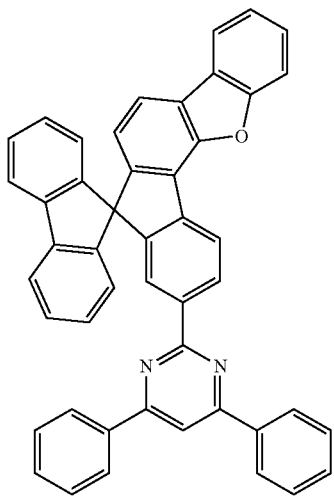
The specific compounds of which the nitrogen-containing heteroaryl is quinoline include the following compounds, but are not limited thereto:
C-93
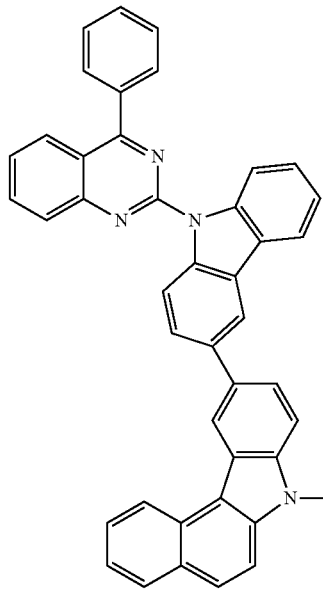
C-94
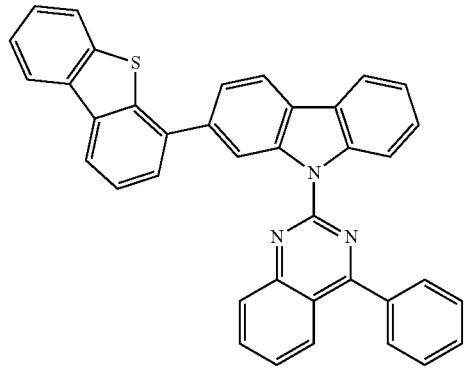
C-95
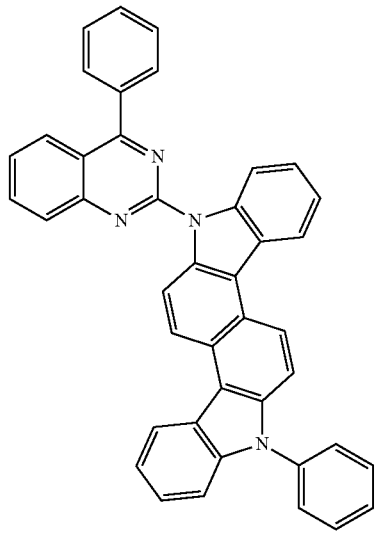

C-96
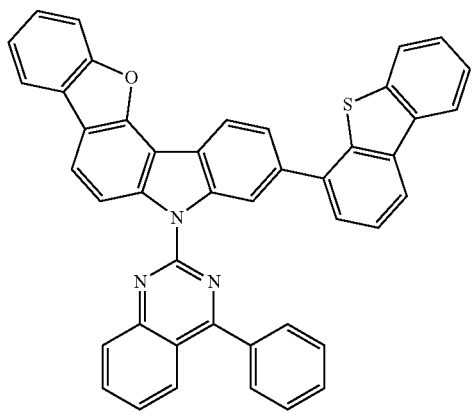
C-99
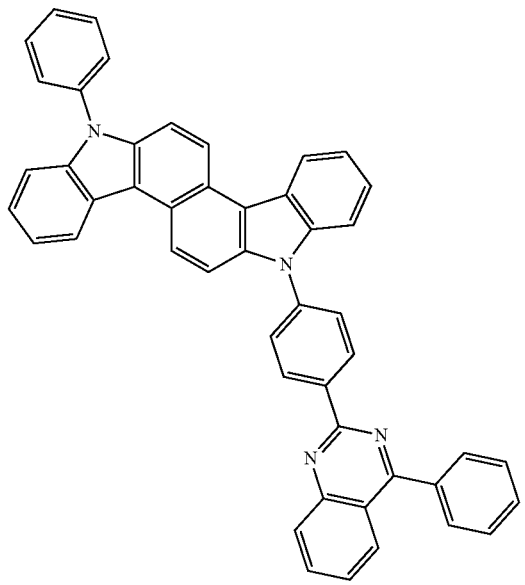
C-97
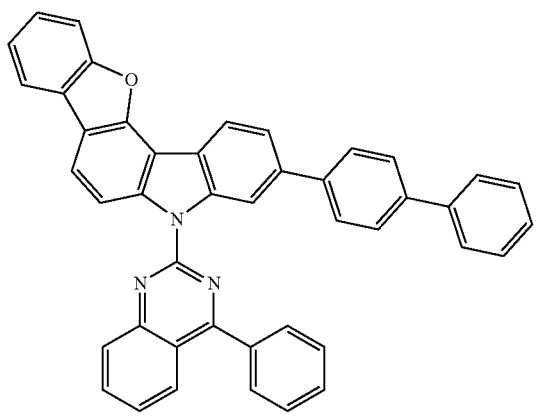
C-100
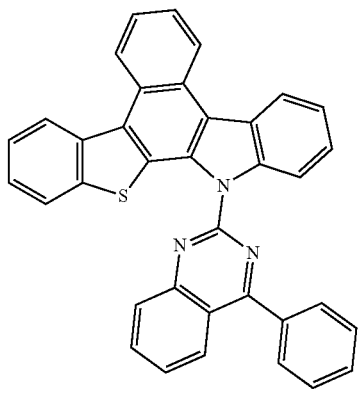
C-98
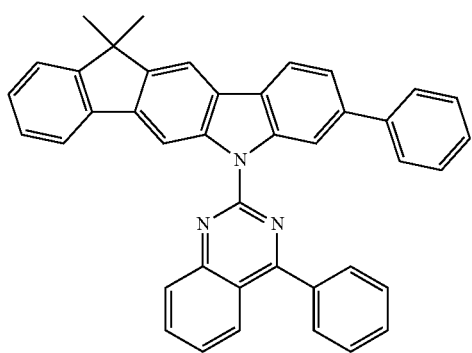
C-101
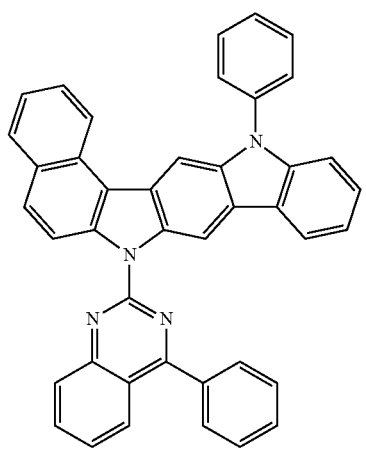

C-102
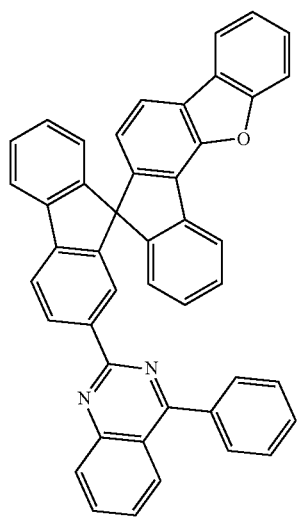
C-103
C-104
C-105
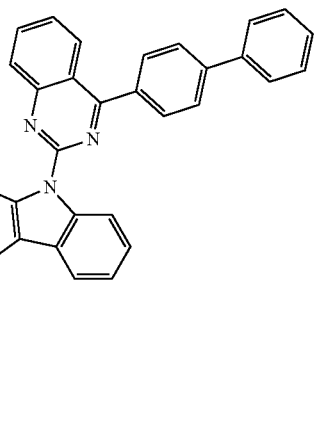
C-106
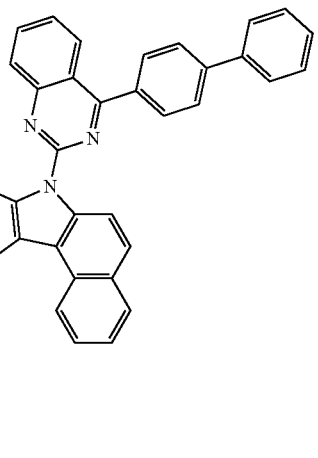
C-107
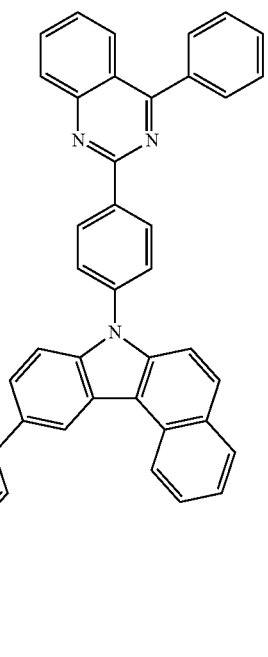

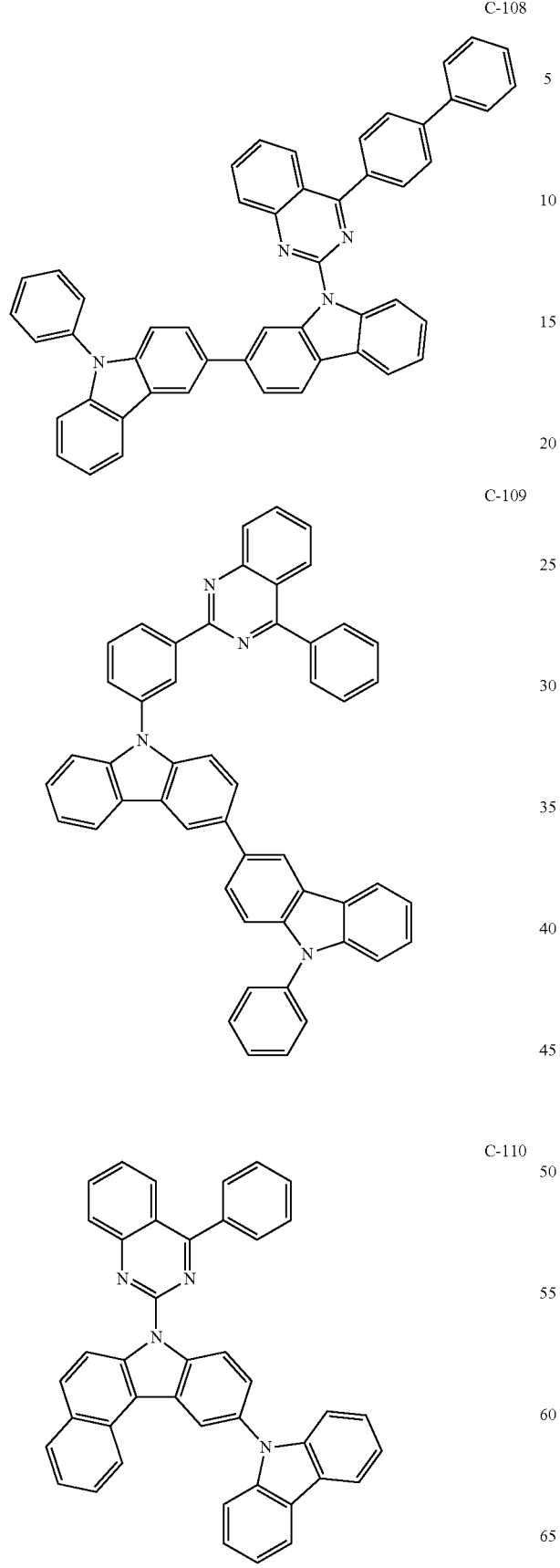
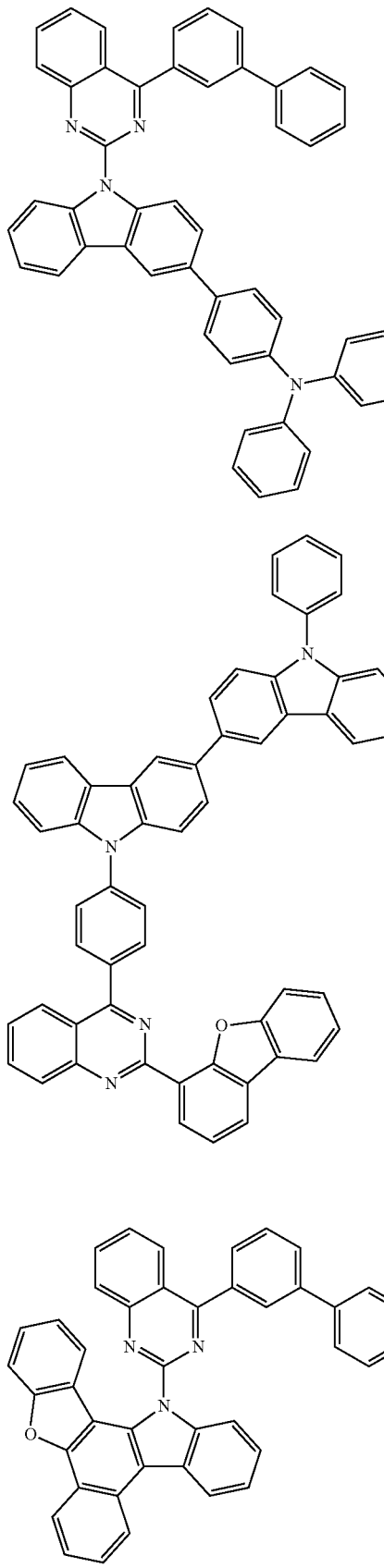

C-114
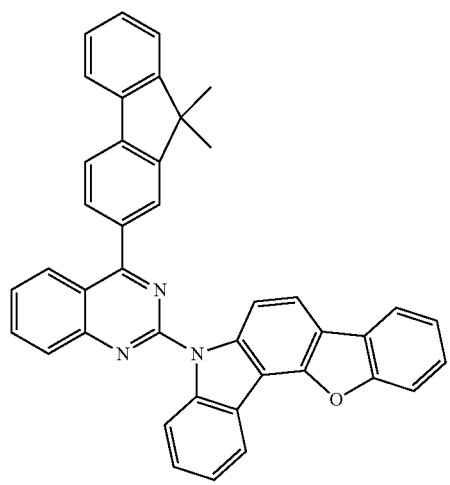
C-117
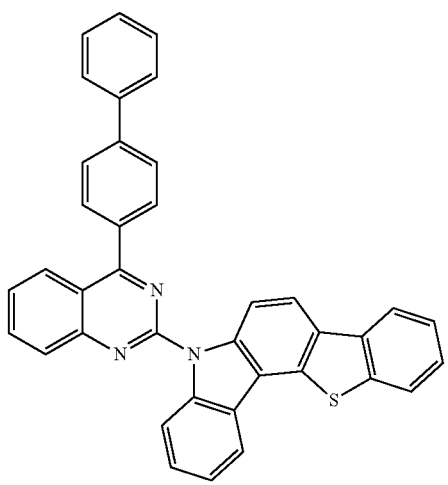
C-115
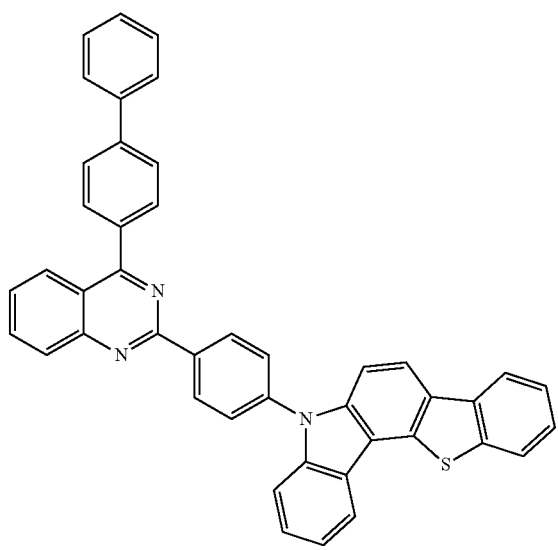
C-118
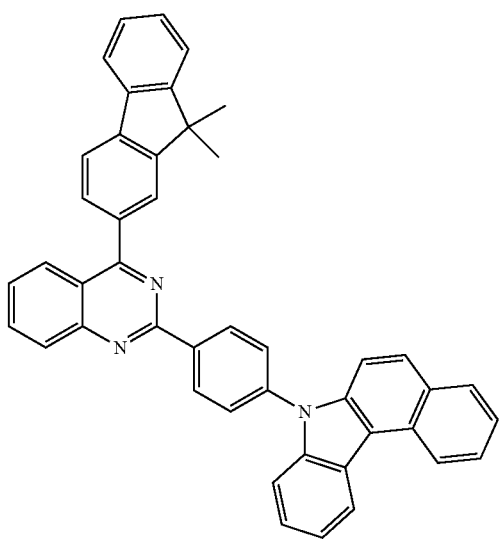
C-116
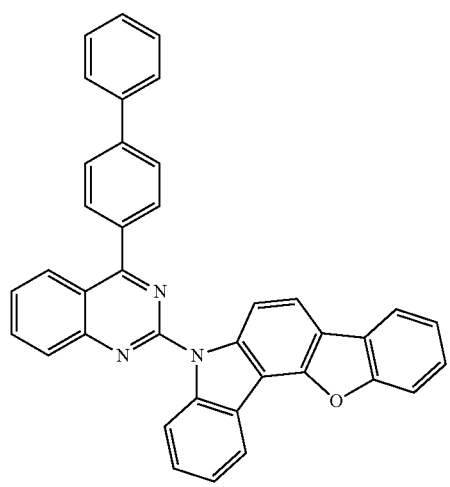
C-119
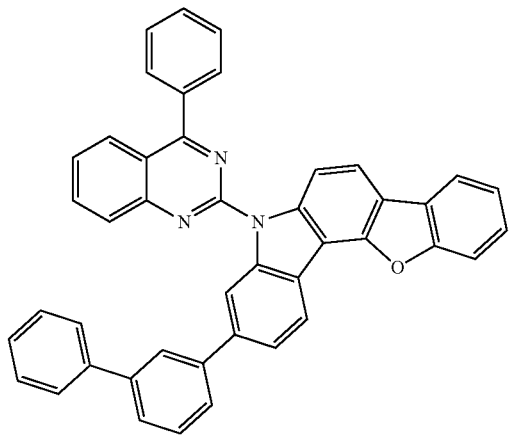

-continued
C-120
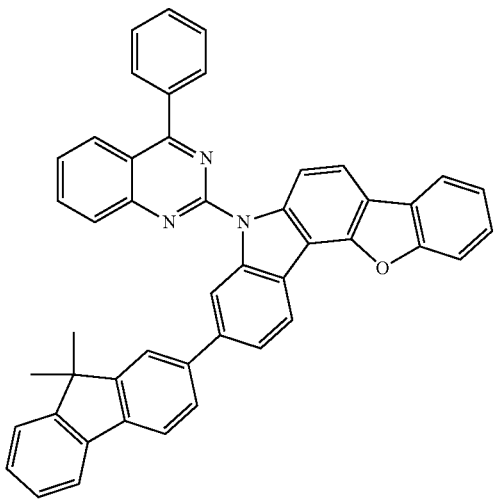
C-121
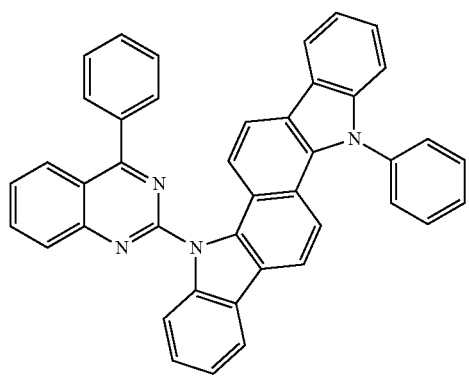
C-122
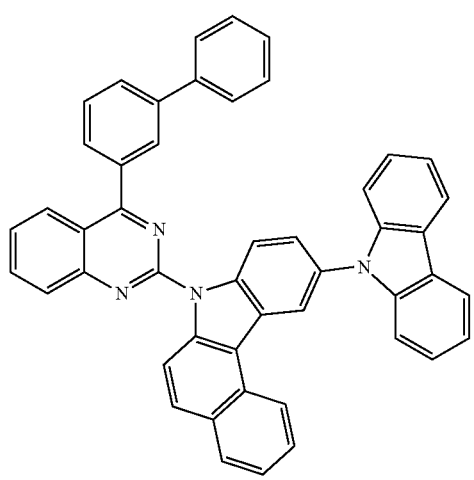
The specific compounds of which the nitrogen-containing heteroaryl is quinoxaline include the following compounds, but are not limited thereto:
C-123
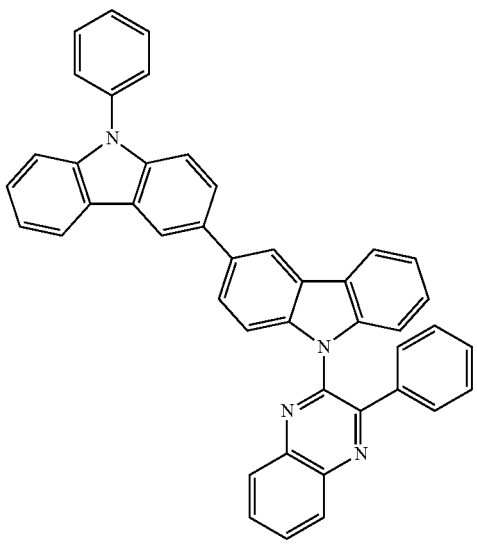
C-124
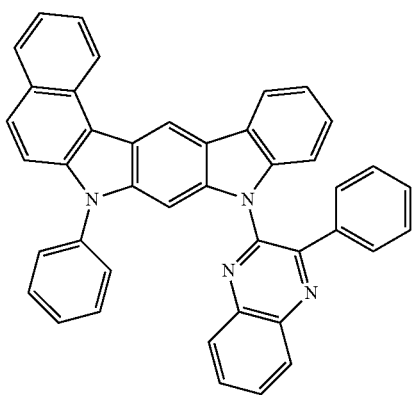
C-125
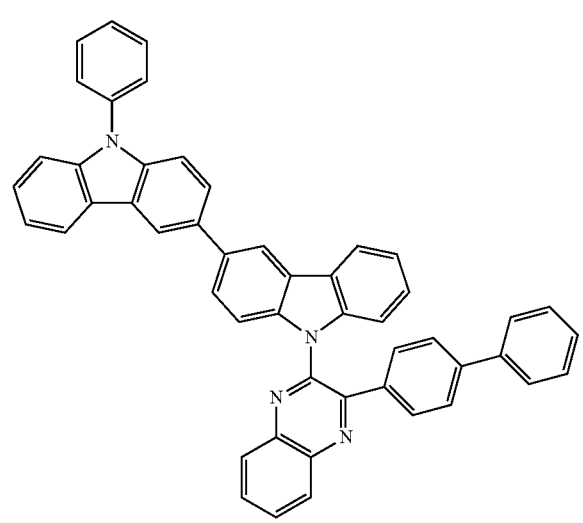

-continued
C-126
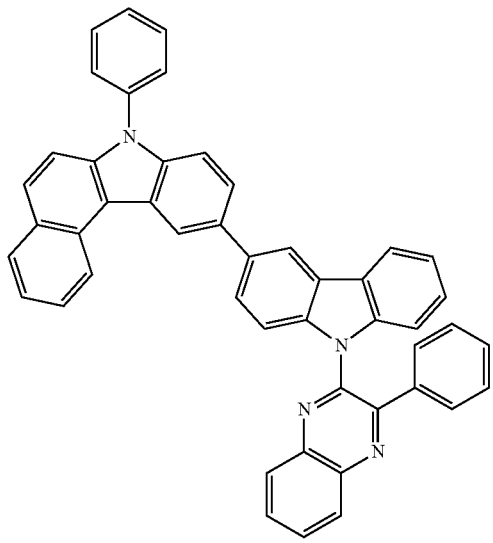
C-127
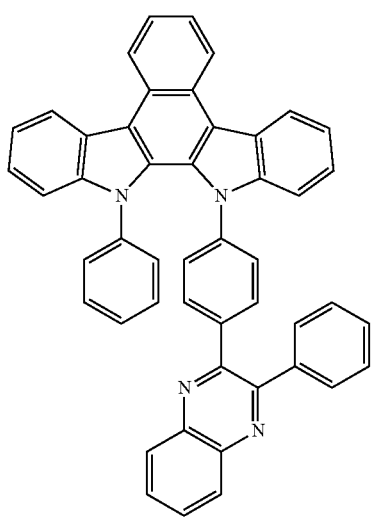
C-128
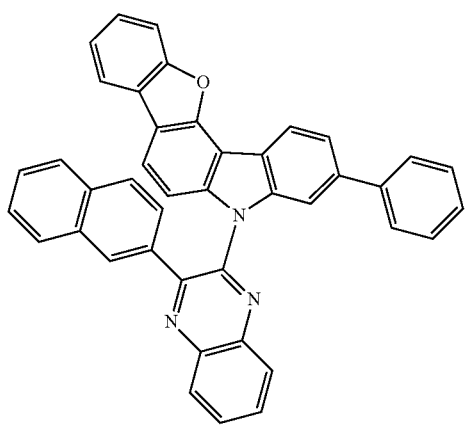
-continued
C-129
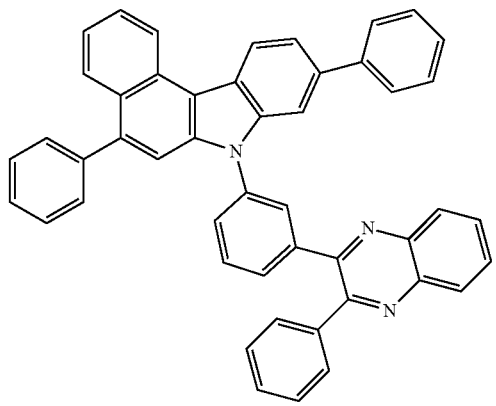
C-130
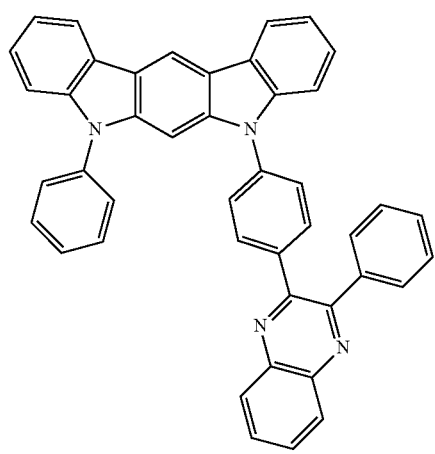
C-131
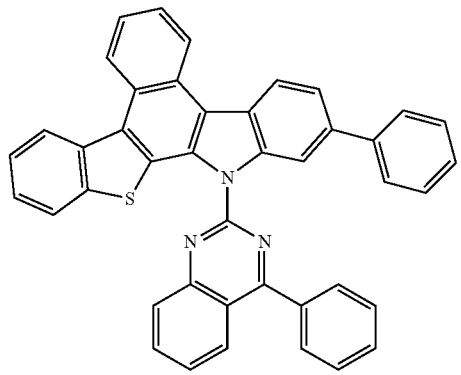

C-132

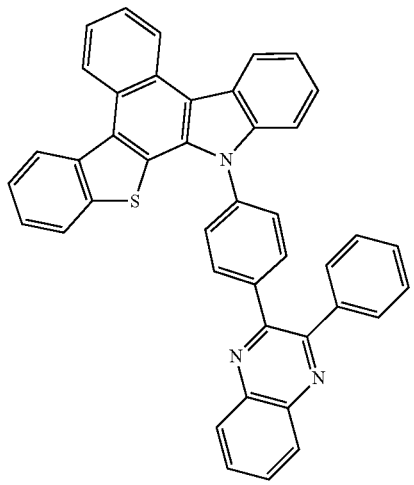

C-133

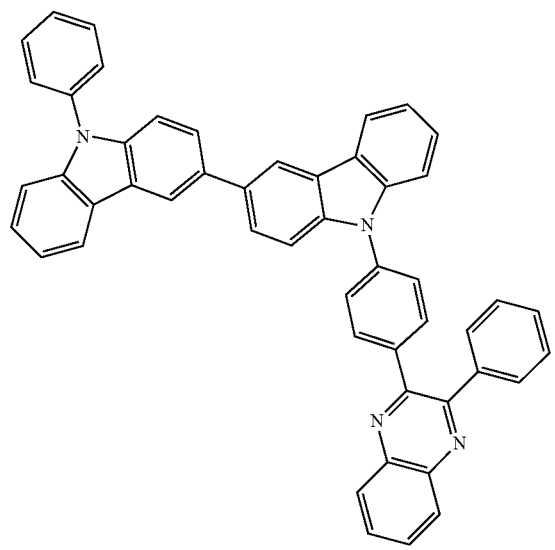

C-134

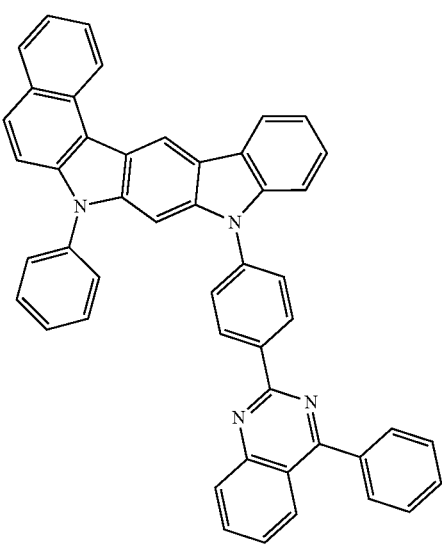

The thickness of the electron buffer layer (126) can be 1 nm or more, but is not limited specifically. In detail, the thickness of the electron buffer layer (126) can be from 2 to 100 nm. The electron buffer layer (126) can be formed on the light-emitting layer (125) in various methods that are known such as vacuum evaporation method, wet film-forming method, laser transfer method, etc.

The light-emitting layer comprised in the organic electroluminescent device of the present invention can comprise a host and a dopant. The host compound can be a phosphorescent host compound or a fluorescent host compound. The dopant compound can be a phosphorescent dopant compound or a fluorescent dopant compound. Preferably, the host compound and the dopant compound can be a fluorescent host compound and a fluorescent dopant compound, respectively.

Anthracene derivatives, aluminum complexes, rubrene derivatives, arylamine derivatives, etc., can be used as a host material, and preferably, anthracene derivatives.

Examples of the host materials of the present invention include the following compounds, but are not limited thereto:

H-1

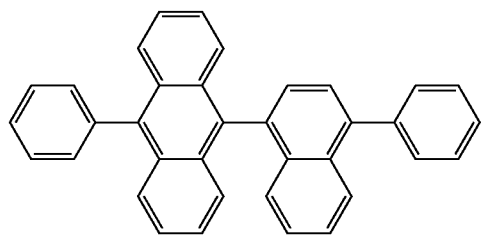

H-2

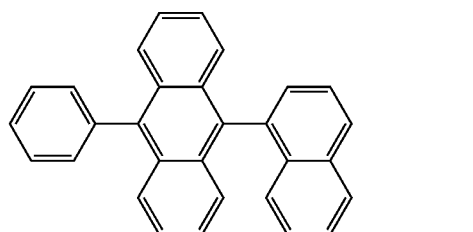

H-3

-continued
H-4
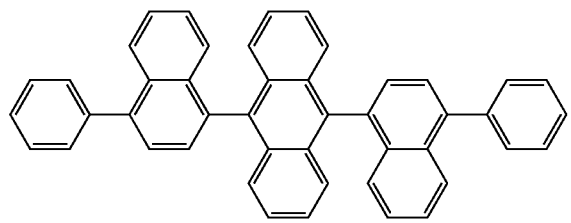
H-5
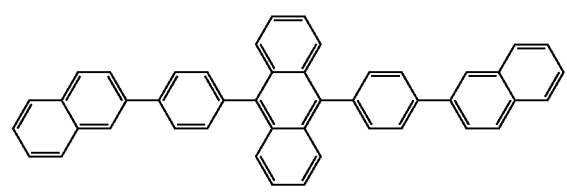
H-6
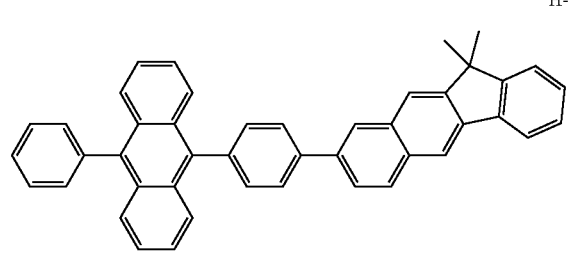
H-7
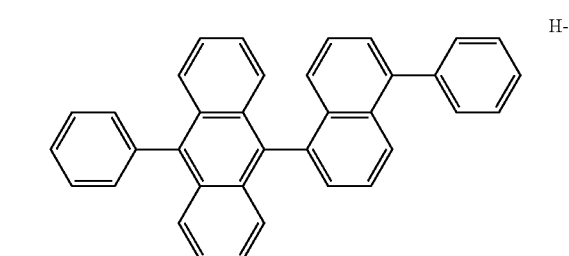
H-8
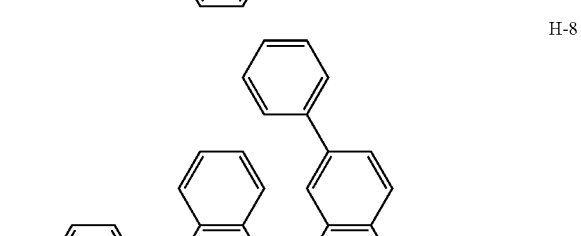
H-9
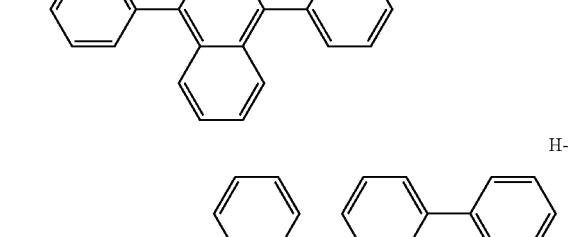
-continued
H-10
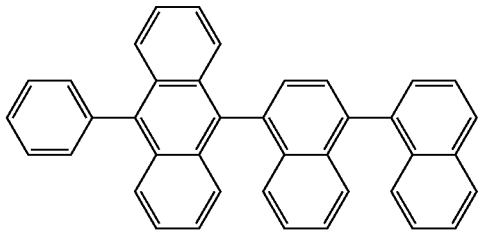
H-11
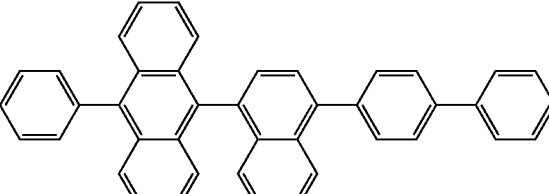
H-12
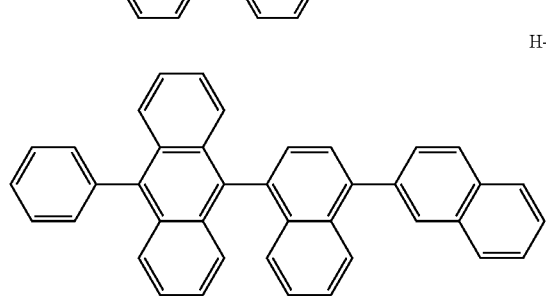
H-13
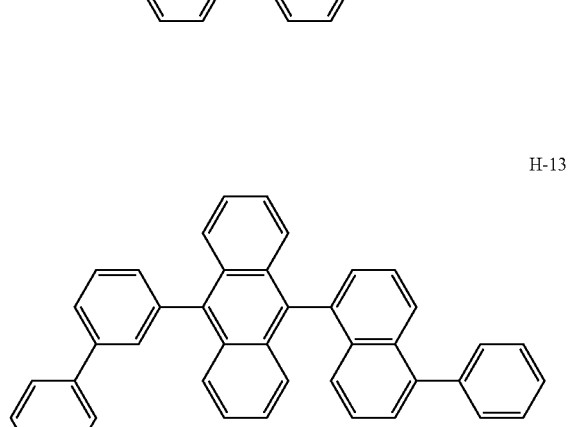
H-14
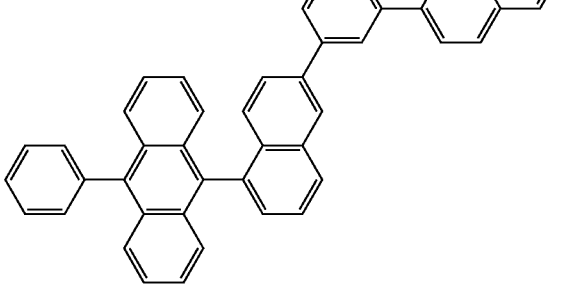

H-15
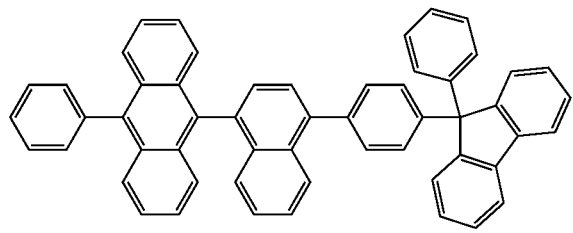
H-16
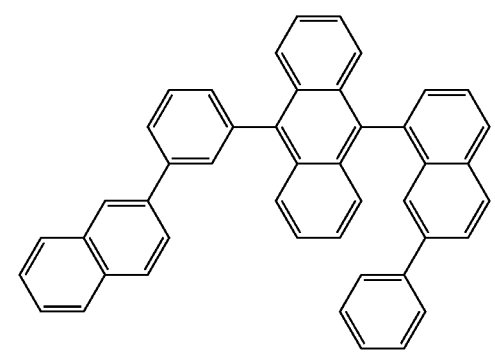
H-17
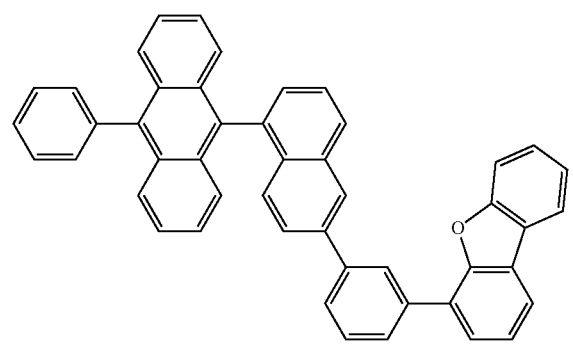
H-18
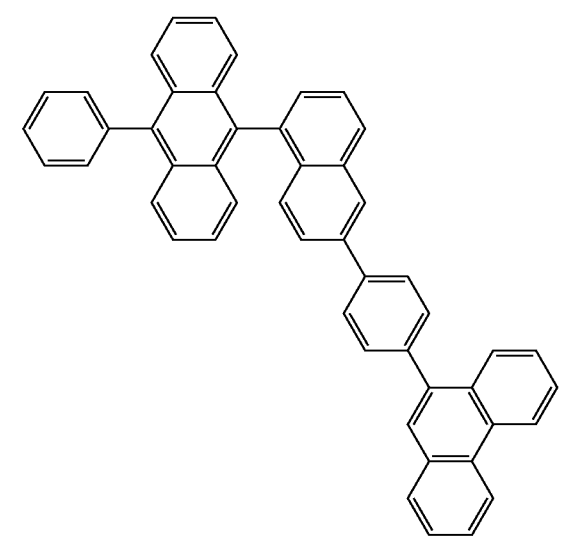
H-19
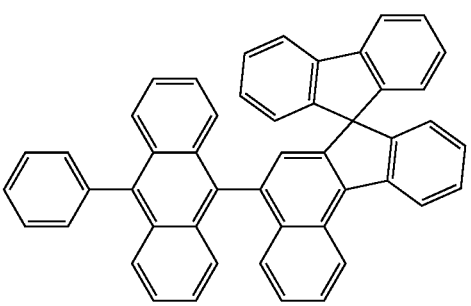
H-20
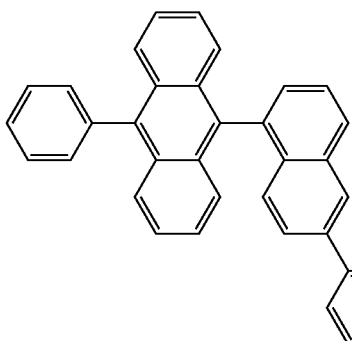
H-21
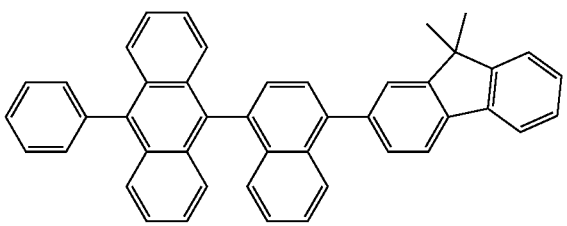
H-22
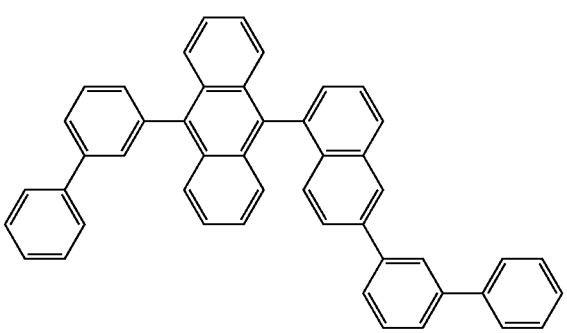

H-23
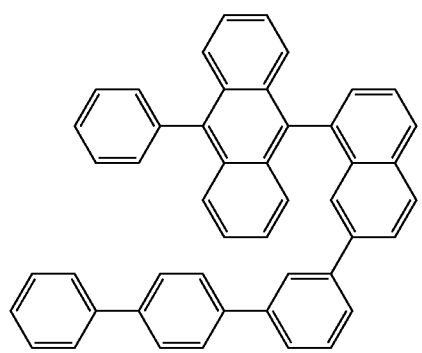
H-24
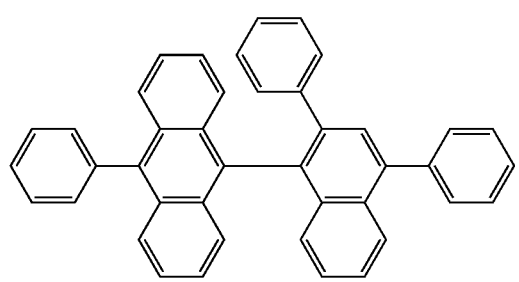
H-25
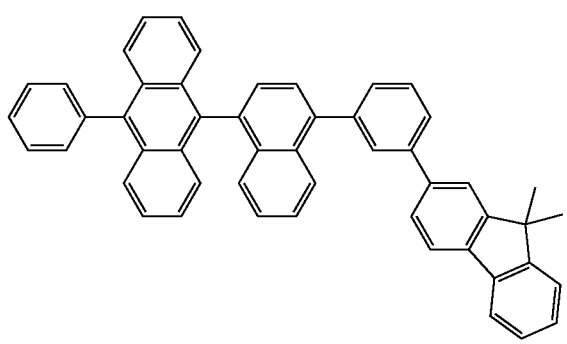
Pyrene-based derivatives, aminofluorene-based derivatives, aminoanthracene-based derivatives, aminochrysene-based derivatives, etc., and preferably, pyrene-based derivatives can be used as a dopant material.
Examples of the dopant materials of the present invention include the following compounds, but are not limited thereto:
D-1
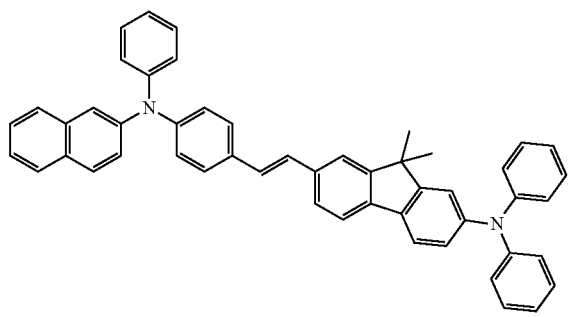
D-2
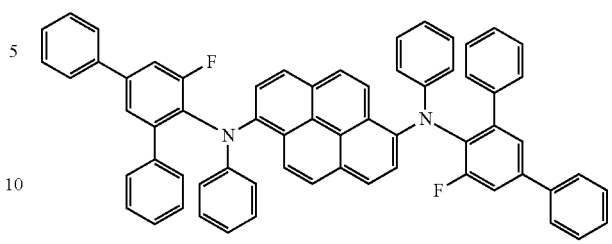
D-3
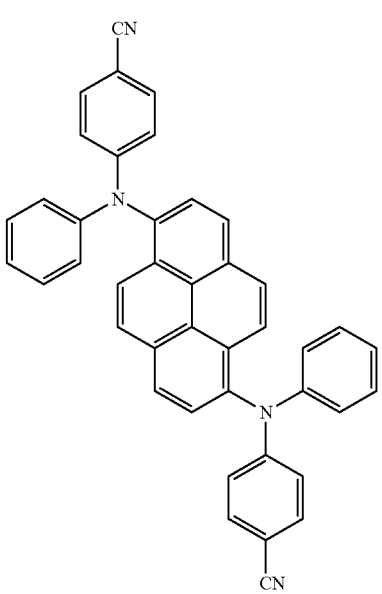
D-4
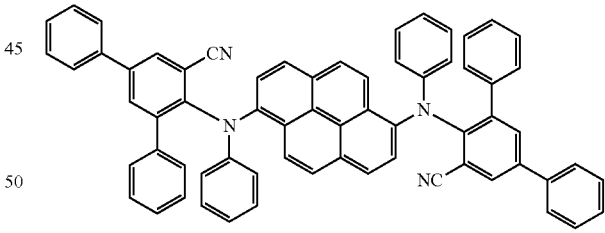
D-5
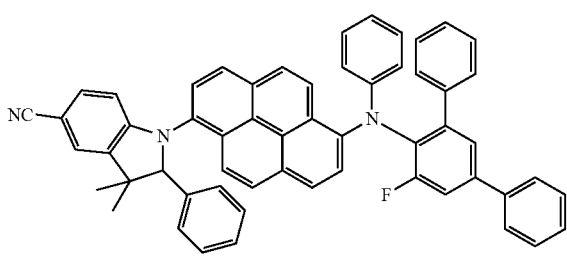

-continued
D-6
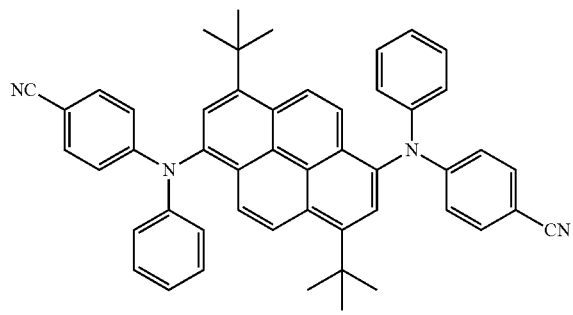
D-7
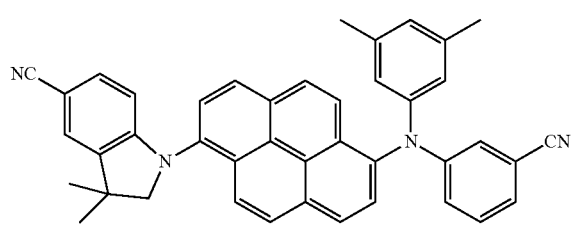
D-8
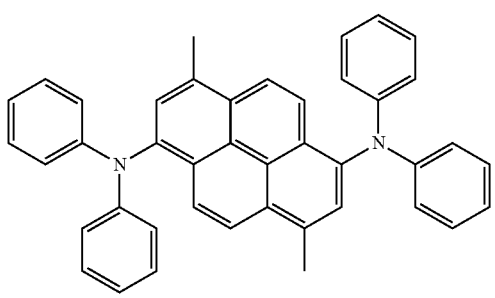
D-9
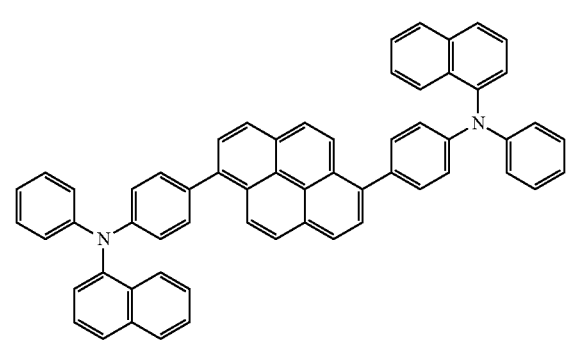
D-10
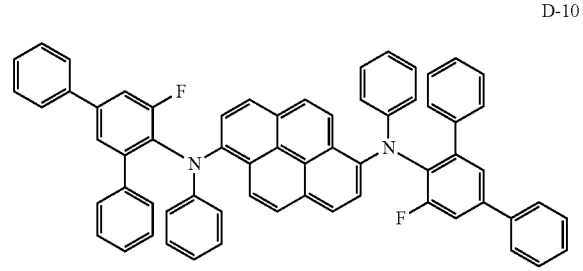
-continued
D-11
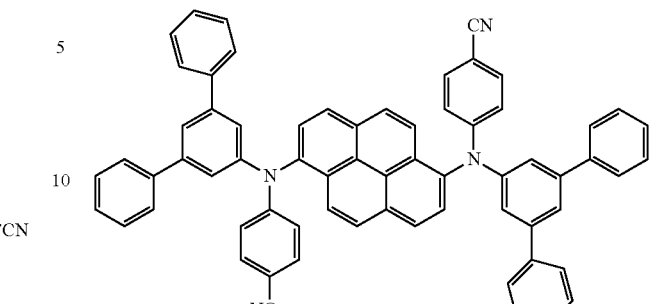
D-12
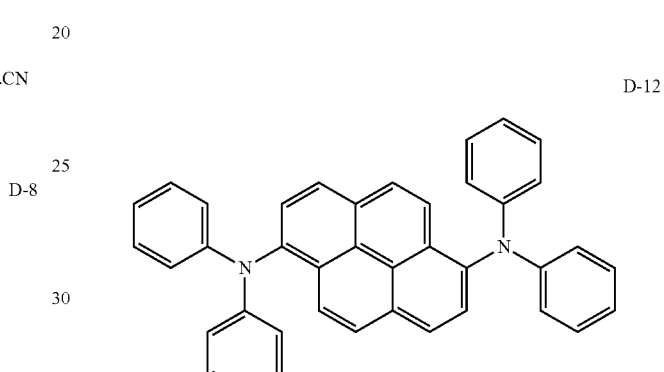
D-13
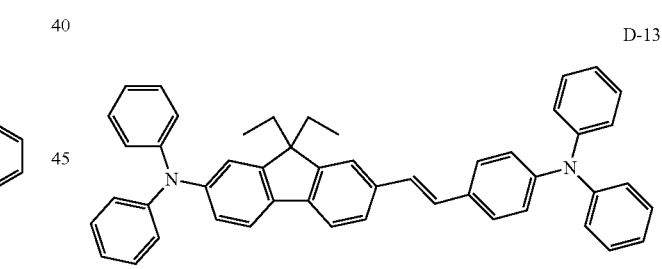
D-14
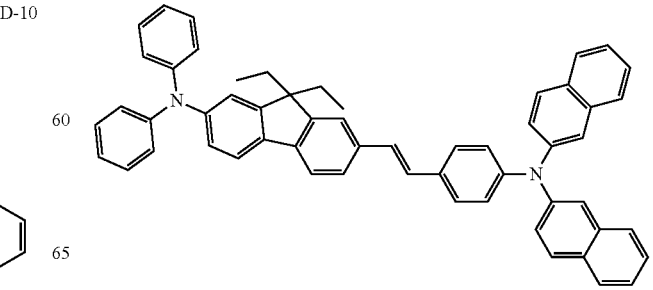

D-15

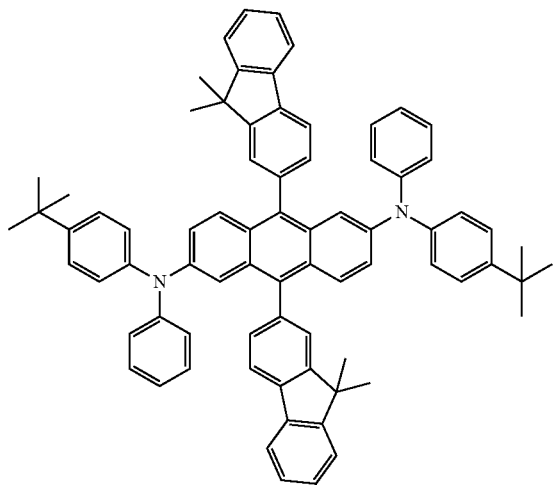

When the light-emitting layer (125) comprises a host and a dopant, the dopant can be doped in an amount of less than about 25 wt %, preferably less than about 17 wt %, based on the total amount of the dopant and host of the light-emitting layer. The thickness of the light-emitting layer (125) can be from about 5 nm to 100 nm, preferably from about 10 nm to 60 nm. Light emission occurs at the light-emitting layer, and the light-emitting layer can be a mono- or multi-layer. When the light-emitting layer (125) is a multi-layer of two or more layers, each light-emitting layer can emit different colors of light. For example, a white light-emitting device can be produced by forming three light-emitting layers (125) that emit blue, red, and green, respectively. The light-emitting layer (125) can be formed on the hole transport layer (123) in various methods that are known such as vacuum evaporation method, wet film-forming method, laser transfer method, etc.

The organic electroluminescent device of the present invention may additionally comprises a hole injection layer or a hole transport layer between the first electrode and the light-emitting layer.

Hereafter, the structure and preparation method of the organic electroluminescent device will be explained with reference to FIG. 1.

In FIG. 1, the organic electroluminescent device (100) comprises a substrate (101), a first electrode (110) formed on the substrate (101), an organic layer (120) formed on the first electrode (110), and a second electrode (130) facing the first electrode (110) formed on the organic layer (120).

The organic layer (120) comprises a hole injection layer (122), a hole transport layer (123) formed on the hole injection layer (122), a light-emitting layer (125) formed on the hole transport layer (123), an electron buffer layer (126) formed on the light-emitting layer (125), and an electron transport zone (129) formed on the electron buffer layer (126). The electron transport zone (129) comprises an electron transport layer (127) formed on the electron buffer layer (126), and an electron injection layer (128) formed on the electron transport layer (127).

The substrate (101) can be a glass substrate, a plastic substrate, or a metal substrate used in a general organic electroluminescent device.

The first electrode (110) can be an anode, and can be formed by a material which has high work function. Materials for the first electrode (110) can be indium tin oxide (ITO), tin oxide (TO), indium zinc oxide (IZO), indium tin zinc oxide (ITZO), or a mixture thereof. The first electrode (110) can be formed in various methods that are known such as evaporation method, sputtering method, etc.

Materials used in the hole injection layer (122) can be known hole injection materials. For example, phthalocyanine compounds such as copper phthalocyanine, MTDATA (4,4',4"-tris[(3-methylphenyl)phenylamino]triphenylamine), 2-TNATA (4,4',4"-tris[2-naphthyl(phenyl)amino]triphenylamine), $N^1,N^{1'}$-([1,1'-biphenyl]-4,4'-diyl)bis($N^1$-(naphthalen-1-yl)-$N^4$,$N^4$-diphenylbenzene-1,4-diamine), Pani/DBSA (polyaniline/dodecylbenzenesulfonic acid), PEDOT/PSS (poly(3,4-ethylenedioxythiophene)/poly(4-styrenesulfonate)), Pani/CSA (polyaniline/camphorsulfonic acid), or Pani/PSS (polyaniline)/poly(4-styrenesulfonate)) can be used, but are not limited thereto.

In addition, the hole injection layer (122) can be formed by using the following compound of formula 11:

(11)

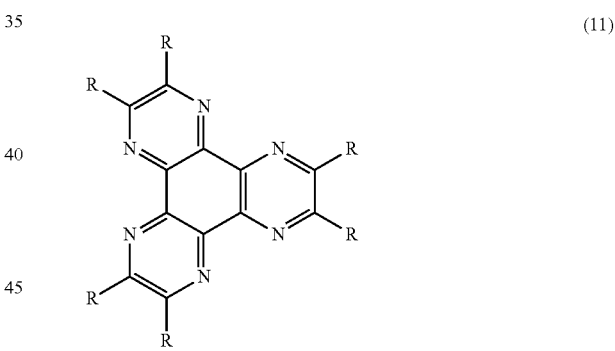

wherein R is selected from a group consisting of a cyano (—CN), a nitro (—$NO_2$), phenylsulfonyl (—$SO_2(C_6H_5)$), a (C2-C5)alkenyl substituted with cyano or nitro, and a phenyl substituted with cyano or nitro.

The compound of formula 11 has a characteristic of being crystallized. Accordingly, the hole injection layer (122) can obtain strength by using the compound.

The hole injection layer (122) can be a mono- or multi-layer. When the hole injection layer (122) is a multi-layer of two or more layers, the compound of formula 11 can be used in one of them. The thickness of the hole injection layer (122) can be from about 1 nm to about 1,000 nm, preferably from about 5 nm to 100 nm. The hole injection layer (122) can be formed on the first electrode (110) in various methods that are known such as vacuum evaporation method, wet film-forming method, laser transfer method, etc.

Examples of the hole injection material comprised in the hole injection layer include the following compounds, but are not limited thereto:

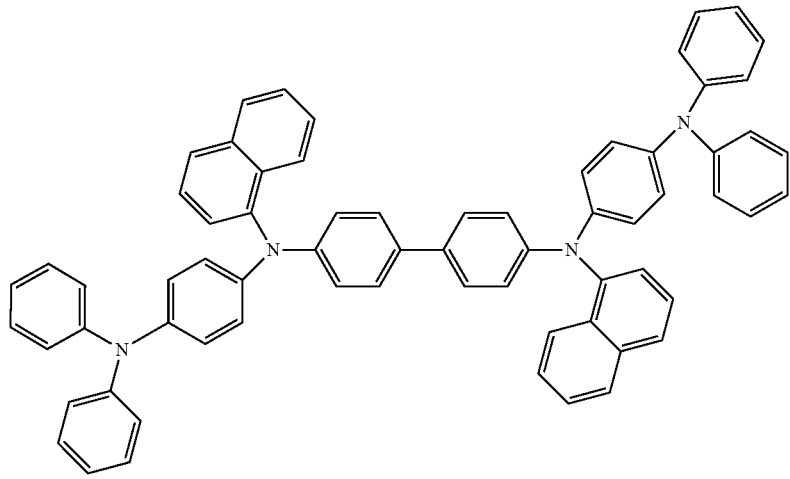

HI-1

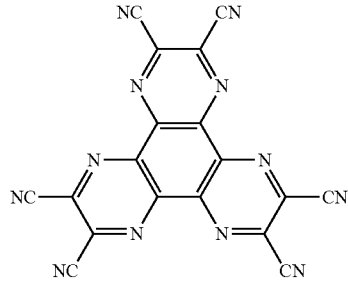

HI-2

Materials used in the hole transport layer (123) can be known hole transport materials. For example, aromatic amine-based derivatives, specifically biphenyl diamine-based derivatives such as TPD(N,N'-bis-(3-methylphenyl)-N,N'-diphenylbenzydine), $N^4,N^4,N^{4'},N^{4'}$-tetra([1,1'-biphenyl]-4-yl-[1,1'-biphenyl]-4,4'-diamine can be used, but are not limited thereto.

Examples of the hole transport material comprised in the hole transport layer include the following compounds, but are not limited thereto:

-continued

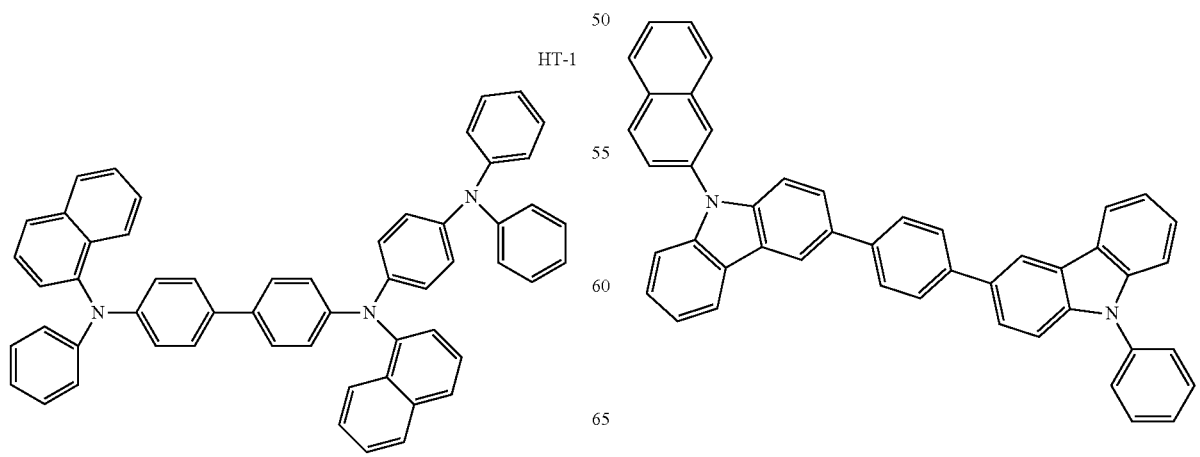

HT-1

HT-2

-continued

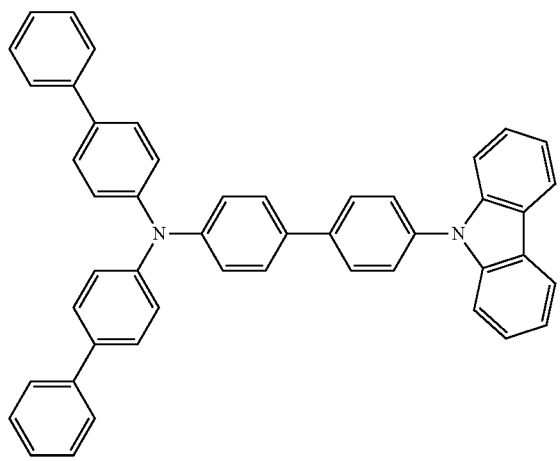

HT-3

The hole transport layer (123) can be a mono- or multi-layer. The thickness of the hole transport layer (123) can be from about 1 nm to about 100 nm, preferably from about 5 nm to 80 nm. The hole transport layer (123) can be formed on the hole injection layer (122) in various methods that are known such as vacuum evaporation method, wet film-forming method, laser transfer method, etc.

When using a material of which HOMO characteristics and anion stability are improved as a hole transport material, the lifespan of the device becomes longer due to stabilized hole transport layer even for organic electroluminescent devices comprising an electron buffer layer of which lifespan is relatively short, i.e. upon comparing using a material of which HOMO characteristics and anion stability are improved to using a material of which HOMO characteristics and anion stability are vulnerable for a hole transport material of the hole transport layer, lifespan characteristics can be prevented from being decreased by using a material of which HOMO characteristics and anion stability are improved, due to relatively low deviation of lifespan according to the material groups consisting of the electron buffer layer even for a device comprising an electron buffer layer of which lifespan is relatively short.

Materials used in the electron transport layer (127) can be known electron transport materials. For example, oxazole-based compounds, isoxazole-based compounds, triazole-based compounds, isothiazole-based compounds, oxadiazole-based compounds, thiadiazole-based compounds, perylene-based compounds, anthracene-based compounds, aluminum complexes, gallium complexes, etc., can be used, but are not limited thereto.

Examples of the electron transport material comprised in the electron transport layer include the following compounds, but are not limited thereto:

ETL-1

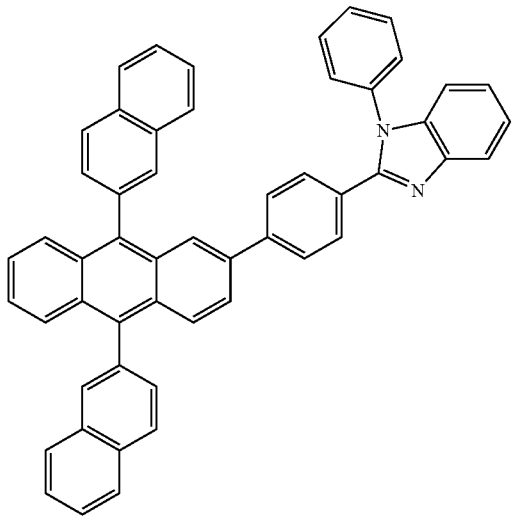

ETL-2

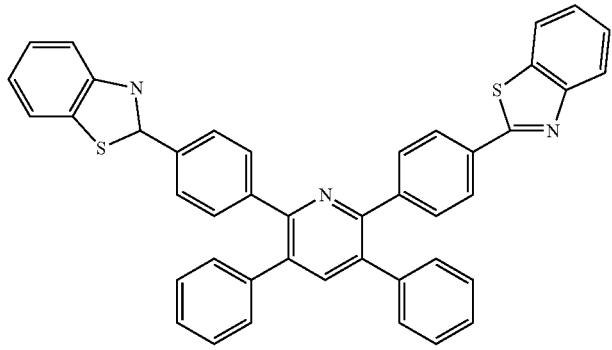

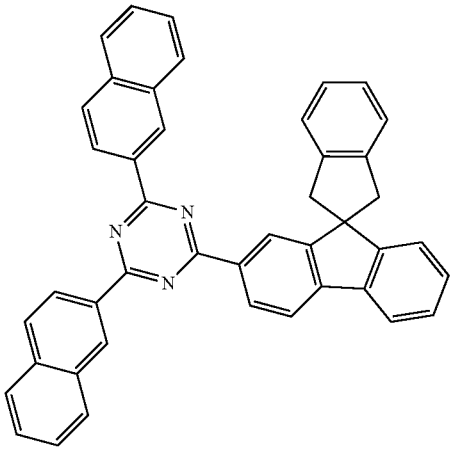

ETL-3

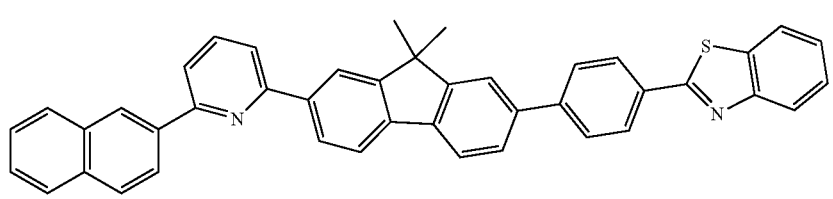

ETL-4

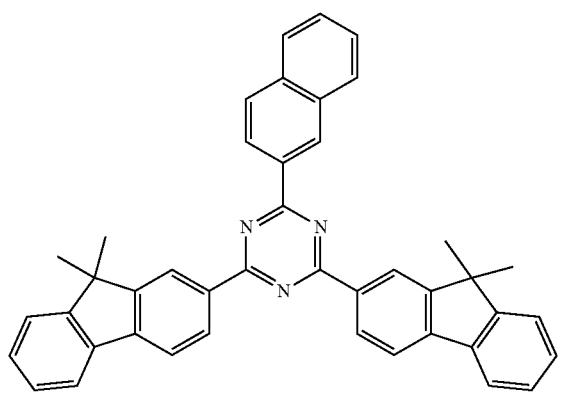

ETL-5

Preferably, the electron transport layer (127) can be a mixed layer comprising an electron transport compound and a reductive dopant. When formed as a mixed layer, the electron transport compound reduces to an anion so that electrons can be easily injected and transported to a light-emitting medium.

When the electron transport layer (127) is formed as a mixed layer, the electron transport compound is not specifically limited, and the known electron transport material can be used.

The reductive dopant can be alkali metals, alkali metal compounds, alkaline-earth metals, rare earth metals, halides thereof, oxides thereof, and complexes thereof. Specific examples of the reductive dopant include lithium quinolate, sodium quinolate, cesium quinolate, potassium quinolate, LiF, NaCl, CsF, $Li_2O$, BaO, and $BaF_2$, but are not limited thereto.

The thickness of the electron transport layer (127) can be from about 5 nm to about 100 nm, preferably from about 10 nm to about 60 nm. The electron transport layer (127) can be formed on the electron buffer layer (126) in various methods that are known such as vacuum evaporation method, wet film-forming method, laser transfer method, etc.

Materials used in the electron injection layer (128) can be known electron injection materials. For example, lithium quinolate, sodium quinolate, cesium quinolate, potassium quinolate, LiF, NaCl, CsF, $Li_2O$, BaO, $BaF_2$, etc., can be used, but are not limited thereto.

The thickness of the electron injection layer (128) can be from about 0.1 to about 10 nm, and preferably from about 0.3 nm to about 9 nm. The electron injection layer (128) can be formed on the electron transport layer (127) in various methods that are known such as vacuum evaporation method, wet film-forming method, laser transfer method, etc.

Lithium quinoline complex metal can be used as the electron injection material comprised in the electron injection layer. Specifically, it can be exemplified as the following compound, but is not limited thereto.

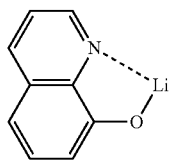

EIL-1

The second electrode (130) can be a cathode, and can be formed by a material which has low work function. Materials for the second electrode (130) can be aluminum (Al), calcium (Ca), magnesium (Mg), silver (Ag), cesium (Cs), lithium (Li), or a combination thereof. The second electrode (130) can be formed in various methods that are known such as evaporation method, sputtering method, etc.

The organic electroluminescent device of FIG. 1 is only an embodiment to be explained clearly, and the present invention should not be limited to the embodiment but can be varied to another mode. For example, an optional component of the organic electroluminescent device of FIG. 1 besides a light-emitting layer and an electron buffer layer can be omitted such as the hole injection layer. In addition, an optional component can be further added. Examples of the further added optional component are impurity layers such as n-doping layer and p-doping layer. Moreover, the organic electroluminescent device can emit light from both sides by placing a light-emitting layer each in both sides in between the impurity layers. The light-emitting layers of both sides can emit different colors. In addition, the first electrode can be a transparent electrode and the second electrode can be a reflective electrode so that the organic electroluminescent device can be a bottom emission type, and the first electrode can be a reflective electrode and the second electrode can be a transparent electrode so that the organic electroluminescent device can be a top emission type. Also, a cathode, an electron transport layer, a light-emitting layer, a hole transport layer, a hole injection layer, and an anode can be sequentially stacked on a substrate to be an inverted organic electroluminescent device.

FIG. 2 illustrates an energy gap relationship among the layers of the organic electroluminescent device according to one embodiment of the present invention.

In FIG. 2, a hole transport layer (123), a light-emitting layer (125), an electron buffer layer (126), and an electron transport zone (129) are sequentially stacked, and electrons are injected from the cathode to the light-emitting layer (125) through the electron transport zone (129) and the electron buffer layer (126).

The LUMO energy level of the electron buffer layer (126) is higher than that of the host compound and the dopant compound of the light-emitting layer (125), and that of the electron transport layer (127). Specifically, LUMO energy levels have the following equational relationship: electron buffer layer>electron transport zone>host compound. According to conventional techniques, the light-emitting area of the light-emitting layer (125) has been shifted to the hole transport layer (123) side due to hole trap and emitted light at the interface. However, according to the present invention, the electron buffer layer (126) has a LUMO energy level as described above to allow an electron trap to occur so that the light-emitting area of the light-emitting layer shifts to the electron transport zone (129) side, thus the lifespan and efficiency of the organic electroluminescent device can be improved. Meanwhile, the HOMO energy level of the electron buffer layer (126) is higher than that of the dopant compound of the light-emitting layer (125), but is lower than that of the host compound and the electron transport zone (129).

The LUMO energy levels of the present invention can be easily measured by known various methods. Generally, LUMO energy levels are measured by cyclic voltammetry or ultraviolet photoelectron spectroscopy (UPS). Therefore, a person skilled in the art can easily comprehend the electron buffer layer, host material, and electron transport zone that satisfy the equational relationship of the LUMO energy levels of the present invention, and practice the present invention. HOMO energy levels can be easily measured by the same method of measuring LUMO energy levels.

According to one embodiment of the organic electroluminescent device of the present invention, the LUMO energy level of the host (Ah) is higher than that of the dopant (Ad).

According to one embodiment of the organic electroluminescent device of the present invention, the LUMO energy level of the electron buffer layer (Ab) is higher than that of the host (Ah).

According to one embodiment of the organic electroluminescent device of the present invention, the LUMO energy level of the electron buffer layer and the LUMO energy level of the host (Ah) have the following equational relationship:

$Ab \leq Ah+0.5$ eV

In order to enhance the luminous efficiency of the device, the LUMO energy level of the electron buffer layer (Ab) can be set to have the following equational relationship:

$Ab < Ah+0.2$~$0.3$ eV

In addition, in order to enhance the lifespan of the device, the LUMO energy level of the electron buffer layer (Ab) can be set to have the following equational relationship:

$Ab < Ah+0.3$~$0.5$ eV

In addition, in order to enhance both efficiency and lifespan of the device, the LUMO energy level of the electron buffer layer (Ab) can be set to have the following equational relationship:

$Ab < Ah+0.3$ eV

Values measured by density functional theory (DFT) are used for the LUMO energy level of the electron buffer layer. The results according to the relationship of the LUMO energy level of the electron buffer layer (Ab) and that of the host (Ah) are for explaining the rough tendency of the device in accordance with the overall LUMO energy groups of the electron buffer layer, and so other results than the above can appear according to the inherent property of the specific derivatives, and the stability of the materials.

The electron buffer layer can be comprised in organic electroluminescent devices emitting every color including blue, red, and green. Preferably, it can be comprised in an organic electroluminescent device emitting blue light (i.e. the main peak wavelength is from 430 to 470 nm, preferably, in the 450's nm).

Hereinafter, the luminescent properties of the organic electroluminescent device according to the present invention will be explained in detail with reference to the following examples.

Examples 1 to 3: Organic Electroluminescent Device Comprising an Electron Buffering Material Comprising a Triazine Derivative An OLED device of the present invention was produced. A transparent electrode indium tin oxide (ITO) thin film (15

Ω/sq) on a glass substrate for an organic light-emitting diode (OLED) device (Samsung-Corning) was subjected to an ultrasonic washing with acetone, ethanol, and distilled water, sequentially, and then was stored in isopropanol. The ITO substrate was then mounted on a substrate holder of a vacuum vapor depositing apparatus. $N^4,N^{4'}$-diphenyl-$N^4$, $N^{4'}$-bis(9-phenyl-9H-carbazol-3-yl)-[1,1'-biphenyl]-4,4'-diamine was introduced into a cell of said vacuum vapor depositing apparatus, and then the pressure in the chamber of said apparatus was controlled to $10^{-6}$ torr. Thereafter, an electric current was applied to the cell to evaporate the above introduced material, thereby forming a hole injection layer having a thickness of 40 nm on the ITO substrate. 1,4,5,8,9,11-hexaazatriphenylene-hexacarbonitrile was then introduced into another cell of said vacuum vapor depositing apparatus, and was evaporated by applying an electric current to the cell, thereby forming a hole injection layer having a thickness of 5 nm on the hole injection layer. Next, N-([1,1'-biphenyl]-4-yl)-9,9-dimethyl-N-(4-(9-phenyl-9H-carbazol-3-yl)phenyl)-9H-fluorene-2-amine was introduced into another cell of said vacuum vapor depositing apparatus, and was evaporated by applying an electric current to the cell, thereby forming a hole transport layer having a thickness of 25 nm on the hole injection layer. Thereafter, compound H-1 was introduced into one cell of the vacuum vapor depositing apparatus, as a host material, and compound D-2 was introduced into another cell as a dopant. The two materials were evaporated at different rates and were deposited in a doping amount of 2 wt % based on the total amount of the host and dopant to form a light-emitting layer having a thickness of 20 nm on the hole transport layer. 2-(4-(9,10-di(naphthalen-2-yl)anthracen-2-yl)phenyl)-1-phenyl-1H-benzo[d]imidazole was then introduced into one cell and lithium quinolate was introduced into another cell. The two materials were evaporated at the same rate and deposited in a doping amount of 50 wt % each to form an electron transport layer having a thickness of 27 nm on the light-emitting layer. Thereafter, an electron buffer layer having a thickness of 9 nm was inserted between the light-emitting layer and the electron transport layer. After depositing lithium quinolate as an electron injection layer having a thickness of 2 nm on the electron transport layer, an Al cathode having a thickness of 80 nm was then deposited by another vacuum vapor deposition apparatus on the electron injection layer. Thus, an OLED device was produced. All the materials used for producing the OLED device were purified by vacuum sublimation at $10^{-6}$ torr prior to use. The driving voltage based on a luminance of 1,000 nits, luminous efficiency, CIE color coordinate, and lifespan of 10 hours based on a luminance of 2,000 nits and constant-current were measured.

Examples 1 to 3

HI-1(40)/HI-2(5)/HT-1(25)/H-1:D-2(20, 2 wt %)/C-x(9)/ETL-1:EIL-1(27)/EIL-1(2)/Al(80)

Comparative Example 1: Organic Electroluminescent Device not Comprising an Electron Buffering Material An OLED device was produced in the same manner as in Examples 1 to 3, except for increasing the thickness of the electron transport layer to 36 nm instead of forming the electron transport layer of 27 nm and the electron buffer layer of 9 nm.

Comparative Example 1

HI-1(40)/HI-2(5)/HT-1(25)/H-1:D-2(20, 2 wt %)/ETL-1:EIL-1(36)/EIL-1(2)/Al(80)

The measured results of the driving voltage, luminous efficiency, CIE color coordinate, and lifespan of Examples 1 to 3 and Comparative Example 1, and the LUMO and HOMO values of the electron buffer layer are shown in Table 1.

TABLE 1

|  | Electron buffer layer | Voltage (V) | Efficiency (cd/A) | Color coordinate (x) | Color coordinate (y) | Lifespan (10 hr) (%) | LUMO (eV) | HOMO (eV) |
| --- | --- | --- | --- | --- | --- | --- | --- | --- |
| Example 1 | C-13 | 4.1 | 5.4 | 0.140 | 0.089 | 96.8 | 1.78 | 5.31 |
| Example 2 | C-53 | 4.5 | 6.0 | 0.139 | 0.093 | 95.8 | 1.87 | 5.61 |
| Example 3 | C-2 | 4.3 | 5.3 | 0.140 | 0.091 | 96.5 | 1.94 | 5.54 |
| Comparative Example 1 | — | 4.3 | 4.8 | 0.140 | 0.094 | 96.1 |  |  |

In Examples 1 to 3, the LUMO energy levels of the electron buffer layer are in the mid-1.9's eV or higher so that the electron injection barrier at the interface between the light-emitting layer and the electron buffer layer is minimized to show fast electron injection characteristics, while showing similar voltage characteristics compared to Comparative Example 1. In particular, the LUMO energy levels of Examples 1 and 2 maintain 1.8's eV and obtained appropriate electron injection characteristics to show high efficiency. On the contrary, the lifespans of Examples 1 to 3 were similar to Comparative Example 1.

Examples 4 to 7: Organic Electroluminescent Device Comprising an Electron Buffering Material Comprising a Triazine Derivative An OLED device was produced in the same manner as in Examples 1 to 3, except for using different electron buffering materials.

Examples 4 to 7

HI-1(40)/HI-2(5)/HT-1(25)/H-1:D-2(20, 2 wt %)/C-x(9)/ETL-1:EIL-1(27)/EIL-1(2)/Al(80)

The measured results of the driving voltage, luminous efficiency, CIE color coordinate, and lifespan of Examples 4 to 7 and Comparative Example 1, and the LUMO and HOMO values of the electron buffer layer are shown in Table 2.

TABLE 2

| | Electron buffer layer | Voltage (V) | Efficiency (cd/A) | Color coordinate (x) | Color coordinate (y) | Lifespan (10 hr) (%) | LUMO (eV) | HOMO (eV) |
|---|---|---|---|---|---|---|---|---|
| Example 4 | C-16 | 4.7 | 4.2 | 0.140 | 0.092 | 98.2 | 1.95 | 5.11 |
| Example 5 | C-46 | 4.8 | 3.8 | 0.140 | 0.098 | 98.2 | 1.96 | 4.98 |
| Example 6 | C-48 | 5.2 | 3.1 | 0.142 | 0.099 | 98.0 | 1.97 | 4.99 |
| Example 7 | C-9 | 5.0 | 3.8 | 0.140 | 0.093 | 98.4 | 2.00 | 5.23 |
| Comparative Example 1 | — | 4.3 | 4.8 | 0.140 | 0.094 | 96.1 | | |

In Examples 4 to 7, the LUMO energy levels of the electron buffer layer are between the mid- and high 1.9's eV and 2.0 eV so that the electron injection barrier of the interface between the light-emitting layer and the electron buffer layer affects much, and thus showed slow electron injection characteristics compared to Comparative Example 1. However, higher voltage characteristics were shown compared to Comparative Example 1. Accordingly, the injected electrons are not relatively sufficient compared to holes, and the possibility of forming excitons is dropped to show lower efficiency compared to Comparative Example 1. However, longer lifespans were shown compared to Comparative Example 1.

Examples 8 to 12: Organic Electroluminescent Device Comprising an Electron Buffering Material Comprising a Triazine Derivative An OLED device was produced in the same manner as in Examples 1 to 3, except for using different electron buffering materials.

Examples 8 to 12

HI-1(40)/HI-2(5)/HT-1(25)/H-1:D-2(20, 2 wt %)/C-x(9)/ETL-1:EIL-1(27)/EIL-1(2)/Al(80)

The measured results of the driving voltage, luminous efficiency, CIE color coordinate, and lifespan of Examples 8 to 12 and Comparative Example 1, and the LUMO and HOMO values of the electron buffer layer are shown in Table 3.

TABLE 3

| | Electron buffer layer | Voltage (V) | Efficiency (cd/A) | Color coordinate (x) | Color coordinate (y) | Lifespan (10 hr) (%) | LUMO (eV) | HOMO (eV) |
|---|---|---|---|---|---|---|---|---|
| Example 8 | C-3 | 4.7 | 4.9 | 0.140 | 0.096 | 97.9 | 1.90 | 5.16 |
| Example 9 | C-45 | 4.4 | 5.3 | 0.139 | 0.094 | 97.3 | 1.95 | 5.34 |
| Example 10 | C-4 | 4.7 | 4.6 | 0.140 | 0.091 | 98.0 | 1.96 | 5.58 |
| Example 11 | C-5 | 4.8 | 4.5 | 0.140 | 0.093 | 97.8 | 1.96 | 5.48 |
| Example 12 | C-6 | 4.2 | 5.2 | 0.140 | 0.091 | 97.4 | 1.98 | 5.40 |
| Comparative Example 1 | — | 4.3 | 4.8 | 0.140 | 0.094 | 96.1 | | |

In Examples 8 to 12, the LUMO energy levels of the electron buffer layer are formed at the mid-1.9's eV, and a specific level of electron injection barrier is applied so that appropriate electron injection characteristics are shown which satisfy both efficiency and lifespan. Thus, higher efficiency and longer lifespan were shown compared to Comparative Example 1. In particular, excellent lifespan characteristics were shown, i.e. 1.5% or more compared to Comparative Example 1 while showing high efficiency. Using an electron buffer layer comprising a triazine derivative was advantageous for suitable efficiency and lifespan.

Examples 13 to 15: Organic Electroluminescent Device Comprising an Electron Buffering Material Comprising a Pyrimidine Derivative An OLED device was produced in the same manner as in Examples 1 to 3, except for using different electron buffering materials.

Examples 13 to 15

HI-1(40)/HI-2(5)/HT-1(25)/H-1:D-2(20, 2 wt %)/C-x(9)/
ETL-1:EIL-1(27)/EIL-1(2)/Al(80)

The measured results of the driving voltage, luminous efficiency, CIE color coordinate, and lifespan of Examples 13 to 15 and Comparative Example 1, and the LUMO and HOMO values of the electron buffer layer are shown in Table 4.

TABLE 4

|  | Electron buffer layer | Voltage (V) | Efficiency (cd/A) | Color coordinate (x) | Color coordinate (y) | Lifespan (10 hr) (%) | LUMO (eV) | HOMO (eV) |
| --- | --- | --- | --- | --- | --- | --- | --- | --- |
| Example 13 | C-56 | 4.6 | 5.2 | 0.140 | 0.096 | 96.3 | 1.76 | 5.02 |
| Example 14 | C-55 | 4.4 | 5.4 | 0.140 | 0.093 | 97.0 | 1.89 | 5.41 |
| Example 15 | C-74 | 4.5 | 5.3 | 0.140 | 0.089 | 96.5 | 1.94 | 5.45 |
| Comparative Example 1 | — | 4.3 | 4.8 | 0.140 | 0.094 | 96.1 |  |  |

In Examples 13 to 15, the LUMO energy levels of the electron buffer layer are formed in the mid-1.7's to 1.8's eV, and the electron injection barrier of the interface between the light-emitting layer and the electron buffer layer decreased compared to triazine derivatives to produce an organic electroluminescent device having fast voltage characteristics and fairly improved efficiency. However, lifespan was similar or worse compared to Comparative Example 1 and worse than triazine derivatives.

Regarding color coordinate, short wavelength of y-coordinate was shown in Examples 14 and 15 of which the HOMO energy values of the electron buffer layer are relatively high. This is due to excitons being sufficiently bounded within the light-emitting layer for having higher HOMO energy levels of the electron buffer layer than those of the anthracene hosts.

Examples 16 to 18: Organic Electroluminescent Device Comprising an Electron Buffering Material Comprising a Quinazoline or Quinoxaline Derivative An OLED device was produced in the same manner as in Examples 1 to 3, except for using different electron buffering materials.

Examples 16 to 18

HI-1(40)/HI-2(5)/HT-1(25)/H-1:D-2(20, 2 wt %)/C-x(9)/
ETL-1:EIL-1(27)/EIL-1(2)/Al(80)

The measured results of the driving voltage, luminous efficiency, CIE color coordinate, and lifespan of Examples 16 to 18 and Comparative Example 1, and the LUMO and HOMO values of the electron buffer layer are shown in Table 5.

TABLE 5

|  | Electron buffer layer | Voltage (V) | Efficiency (cd/A) | Color coordinate (x) | Color coordinate (y) | Lifespan (10 hr) (%) | LUMO (eV) | HOMO (eV) |
| --- | --- | --- | --- | --- | --- | --- | --- | --- |
| Example 16 | C-93 | 5.5 | 3.7 | 0.146 | 0.108 | 99.0 | 1.93 | 5.05 |
| Example 17 | C-94 | 5.4 | 3.4 | 0.140 | 0.099 | 98.0 | 1.94 | 5.41 |
| Example 18 | C-132 | 5.4 | 3.3 | 0.140 | 0.092 | 97.8 | 2.09 | 5.18 |
| Comparative Example 1 | — | 4.3 | 4.8 | 0.140 | 0.094 | 96.1 |  |  |

In Examples 16 to 18, the LUMO energy levels of the electron buffer layer are maintained in the mid-1.9's to 2.0's eV. Although the LUMO energy levels of some of the electron buffer layers were maintained in the mid-1.9's, the electron injection ability of the quinazoline and quinoxaline derivatives were dropped drastically compared to triazine or pyrimidine derivatives so that a device having slow voltage characteristics and decreased efficiency was produced. On the contrary, higher lifespan characteristics were shown compared to Comparative Example 1. This is due to interfacial light emission between the electron transport layer and the light-emitting layer being mitigated as a result of the decline of electron injection ability caused by the electron buffer layer.

Examples 19 to 22: Comparison of Characteristics According to Existence of Phenyl in Triazine Derivatives An OLED device was produced in the same manner as in Examples 1 to 3, except for using different electron buffering materials.

Examples 19 to 22

HI-1(40)/HI-2(5)/HT-1(25)/H-1:D-2(20, 2 wt %)/C-x(9)/ETL-1:EIL-1(27)/EIL-1(2)/Al(80)

The measured results of the driving voltage, luminous efficiency, CIE color coordinate, and lifespan of Examples 19 to 22, and the LUMO and HOMO values of the electron buffer layer are shown in Table 6.

TABLE 6

| | Electron buffer layer | Voltage (V) | Efficiency (cd/A) | Color coordinate (x) | Color coordinate (y) | Lifespan (10 hr) (%) | LUMO (eV) | HOMO (eV) |
|---|---|---|---|---|---|---|---|---|
| Example 19 | C-25 | 4.8 | 4.4 | 0.140 | 0.093 | 98.0 | 1.97 | 5.33 |
| Example 20 | C-2 | 4.3 | 5.3 | 0.140 | 0.091 | 96.5 | 1.94 | 5.53 |
| Example 21 | C-7 | 4.5 | 5.4 | 0.140 | 0.095 | 96.9 | 1.87 | 5.15 |
| Example 22 | C-1 | 4.8 | 4.5 | 0.140 | 0.095 | 97.8 | 1.95 | 4.98 |

In Examples 19 and 20, characteristics of the device were compared according to existence of phenyl between the carbazole derivative and the triazine derivative. The electron injection was disrupted due to increase of the LUMO energy values of Example 19 compared to Example 20 by inserting a phenyl therebetween. Thus, high driving voltage and low efficiency were shown, but the lifespan improved.

In Examples 21 and 22, characteristics of the device were compared according to existence of phenyl between the carbazole derivative and the triazine derivative. The electron injection was disrupted due to increase of the LUMO energy values of Example 21 compared to Example 22 by inserting a phenyl therebetween. Thus, high driving voltage and low efficiency were shown, but the lifespan improved. In addition, similar tendency was shown regardless of meta or para substitution position of phenyl. However, higher LUMO energy level difference was shown in Example 22 in which substitution was made at the meta position.

Examples 23 to 26: Comparison of Characteristics in Accordance with Using Triazine, Quinazoline, and Quinoxaline Derivatives as an Electron Buffering Material An OLED device was produced in the same manner as in Examples 1 to 3, except for using different electron buffering materials.

Examples 23 to 26

HI-1(40)/HI-2(5)/HT-1(25)/H-1:D-2(20, 2 wt %)/C-x(9)/ETL-1:EIL-1(27)/EIL-1(2)/Al(80)

The measured results of the driving voltage, luminous efficiency, CIE color coordinate, and lifespan of Examples 23 to 26, and the LUMO and HOMO values of the electron buffer layer are shown in Table 7.

TABLE 7

|  | Electron buffer layer | Voltage (V) | Efficiency (cd/A) | Color coordinate (x) | Color coordinate (y) | Lifespan (10 hr) (%) | LUMO (eV) | HOMO (eV) |
| --- | --- | --- | --- | --- | --- | --- | --- | --- |
| Example 23 | C-95 | 5.5 | 3.1 | 0.146 | 0.108 | 97.8 | 1.96 | 4.91 |
| Example 24 | C-44 | 4.5 | 5.0 | 0.140 | 0.093 | 96.1 | 1.90 | 5.08 |
| Example 25 | C-24 | 4.5 | 5.4 | 0.140 | 0.095 | 96.9 | 1.87 | 5.15 |
| Example 26 | C-123 | 5.8 | 2.8 | 0.152 | 0.114 | 96.5 | 2.08 | 5.03 |

In Examples 23 and 24, triazine and quinazoline derivatives determining the LUMO energy level were compared by identically maintaining the derivative of the HOMO orbital zone for checking the device characteristics according to the derivatives determining the LUMO energy level.

In contrast to Example 24 of a triazine derivative, the LUMO energy level increased in that the electron injection was highly disrupted in Example 23 of a quinazoline derivative, and thus showed improved lifespan in spite of high driving voltage and low efficiency.

In Examples 25 and 26, triazine and quinoxaline derivatives determining the LUMO energy level were compared by identically maintaining the derivative of the HOMO orbital zone for checking the device characteristics according to the derivatives determining the LUMO energy level.

In contrast to Example 25 of a triazine derivative, the LUMO energy level increased in that the electron injection was highly disrupted in Example 26 of a quinoxaline derivative, and thus showed improved lifespan in spite of high driving voltage and low efficiency.

In addition, quinazoline and quinoxaline derivatives showed higher x- and y-coordinates compared to triazine derivatives. This is due to the electron injection ability being dropped due to the electron buffer layer, and the HOMO energy level of the electron buffer layer being lower than that of the anthracene host while the light-emitting zone got further from the interface between the electron transport layer and the light-emitting layer so that the excitons were not bounded within the light-emitting layer, and the electron buffer layer contributed to light emission.

Examples 27 to 31 and Comparative Examples 2 to 5: Comparison of Characteristics According to Existence of an Electron Transport Layer within a Constitution Comprising or Non-Comprising an Electron Buffer Layer In Examples 27 to 31, an OLED device comprising an electron buffer layer was produced having the same constitution as in Example 22, except for varying the electron transport layer.

Examples 27 to 31

HI-1(40)/HI-2(5)/HT-1(25)/H-1:D-2(20, 2 wt %)/C-x(9)/ETL:EIL-1(27)/EIL-1(2)/Al(80)

In Comparative Examples 2 to 5, an OLED device not comprising any electron buffer layer was produced having the same constitution as in Comparative Example 1, except for varying the electron transport layer.

Comparative Examples 2 to 5

HI-1(40)/HI-2(5)/HT-1(25)/H-1:D-2(20, 2 wt %)/ETL:EIL-1(36)/EIL-1(2)/Al(80)

The measured results of the driving voltage, luminous efficiency, CIE color coordinate, and lifespan of Comparative Examples 1 to 5 and Examples 27 to 31, and the LUMO and HOMO values of the electron transport layer are shown in Table 8.

TABLE 8

|  | Electron buffer layer | Electron transport layer | Voltage (V) | Efficiency (cd/A) | Color coordinate (x) | Color coordinate (y) | Lifespan (10 hr) (%) | LUMO (eV) | HOMO (eV) |
| --- | --- | --- | --- | --- | --- | --- | --- | --- | --- |
| Comp. Ex. 1 | — | ETL-1 | 4.3 | 4.8 | 0.140 | 0.094 | 96.1 | 1.81 | 5.12 |
| Comp. Ex. 2 | — | ETL-2 | 3.5 | 4.6 | 0.140 | 0.087 | 100.8 | 1.86 | 5.67 |
| Comp. Ex. 3 | — | ETL-3 | 4.1 | 4.6 | 0.140 | 0.087 | 97.0 | 1.92 | 5.89 |
| Comp. Ex. 4 | — | ETL-4 | 4.1 | 6.4 | 0.138 | 0.094 | 87.7 | 1.82 | 5.46 |
| Comp. Ex. 5 | — | ETL-5 | 4.2 | 4.5 | 0.140 | 0.087 | 96.7 | 1.89 | 5.8 |
| Example 27 | C-1 | ETL-1 | 4.7 | 4.3 | 0.140 | 0.093 | 98.5 | 1.81 | 5.12 |
| Example 28 | C-1 | ETL-2 | 4.5 | 4.7 | 0.140 | 0.093 | 98.5 | 1.86 | 5.67 |
| Example 29 | C-1 | ETL-3 | 4.4 | 4.7 | 0.140 | 0.092 | 98.6 | 1.92 | 5.89 |
| Example 30 | C-1 | ETL-4 | 4.8 | 4.7 | 0.140 | 0.093 | 97.6 | 1.82 | 5.46 |
| Example 31 | C-1 | ETL-5 | 4.7 | 4.3 | 0.141 | 0.093 | 98.2 | 1.89 | 5.8 |

In contrast to Comparative Examples 1 to 5, an electron buffer layer of compound C-1 was inserted in Examples 27 to 31, and showed an improvement in lifespan while maintaining appropriate efficiency. The lifespan of Comparative Example 2 showed 100.8%. This is an abnormal result caused by imbalance in formation of excitons in ETL-2 in the device. The electron buffer layer supplemented the result and appropriate efficiency, and lifespan are shown. The tendency with regard to the electron buffer layer was similar even when the electron transport layer was changed to pyridine, triazine, anthracene derivatives, etc.

Comparative Example 6 and Examples 32 to 35:
Organic Electroluminescent Device Comprising a Multi-Layered Hole Transport Layer and Comprising or Non-Comprising an Electron Buffer Layer In Comparative Example 6, an OLED device was produced in the same manner as in Comparative Example 1, except for inserting two separate hole transport layers of 20 nm and 5 nm, respectively, rather than one hole transport layer of 25 nm, and changing the thickness of HI-1 to 60 nm.

Comparative Example 6

HI-1(60)/HI-2(5)/HT-1(20)/HT-2(5)/H-1:D-2(20, 2 wt %)/ETL-1:EIL-1(36)/EIL-1(2)/Al(80)

In Examples 32 to 35, an OLED device comprising an electron buffer layer was produced having the same constitution as in Comparative Example 6, except for varying the electron buffer layer.

Examples 32 to 35

HI-1(60)/HI-2(5)/HT-1(20)/HT-2(5)/H-1:D-2(20, 2 wt %)/C-x(9)/ETL-1(27)/EIL-1(2)/Al(80)

The measured results of the driving voltage, luminous efficiency, CIE color coordinate, and lifespan of Comparative Example 6 and Examples 32 to 35, and the LUMO and HOMO values of the electron buffer layer are shown in Table 9.

In Comparative Example 6, efficiency was increased by inserting hole transport layer 2 which can increase the efficiency by efficiently injecting the holes compared to Comparative Example 1.

In Examples 32 to 35, results in which both efficiency and lifespan were improved were obtained compared to Comparative Example 6 by inserting an electron buffer layer to a constitution having hole transport layer 2.

The tendency with regard to the electron buffer layer was similar even when hole transport layer 2 was inserted.

Comparative Example 7 and Examples 36 to 39:
Organic Electroluminescent Device Comprising a Multi-Layered Hole Transport Layer and Comprising or Non-Comprising an Electron Buffer Layer In Comparative Example 7, an OLED device was produced in the same manner as in Comparative Example 6, except for changing hole transport layer 2 to another derivative.

Comparative Example 7

HI-1(60)/HI-2(5)/HT-1(20)/HT-3(5)/H-1:D-2 (20, 2 wt %)/ETL-1:EIL-1(36)/EIL-1(2)/Al(80)

In Examples 36 to 39, an OLED device comprising an electron buffer layer was produced having the same constitution as in Example 32, except for changing the hole transport layer and the electron buffer layer.

Examples 36 to 39

HI-1(60)/HI-2(5)/HT-1(20)/HT-3(5)/H-1:D-2 (20, 2 wt %)/C-x(9)/ETL-1:EIL-1(27)/EIL-1(2)/Al(80)

The measured results of the driving voltage, luminous efficiency, CIE color coordinate, and lifespan of Comparative Example 7 and Examples 36 to 39, and the LUMO and HOMO values of the electron buffer layer are shown in Table 10.

TABLE 9

| | Hole transport layer 2 | Electron buffer layer | Voltage (V) | Efficiency (cd/A) | Color coordinate (x) | Color coordinate (y) | Lifespan (10 hr) (%) | LUMO (eV) | HOMO (eV) |
|---|---|---|---|---|---|---|---|---|---|
| Comp. Ex. 6 | HT-2 | — | 4.2 | 6.3 | 0.140 | 0.097 | 95.6 | | |
| Example 32 | HT-2 | C-1 | 4.6 | 6.2 | 0.140 | 0.101 | 97.0 | 1.95 | 4.98 |
| Example 33 | HT-2 | C-3 | 4.5 | 6.7 | 0.139 | 0.098 | 96.1 | 1.90 | 5.15 |
| Example 34 | HT-2 | C-5 | 4.5 | 6.4 | 0.139 | 0.095 | 97.1 | 1.96 | 5.48 |
| Example 35 | HT-2 | C-24 | 4.3 | 7.2 | 0.139 | 0.096 | 95.7 | 1.87 | 5.15 |

TABLE 10

| | Hole transport layer 2 | Electron buffer layer | Voltage (V) | Efficiency (cd/A) | Color coordinate (x) | Color coordinate (y) | Lifespan (10 hr) (%) | LUMO (eV) | HOMO (eV) |
|---|---|---|---|---|---|---|---|---|---|
| Comp. Ex. 7 | HT-3 | — | 4.1 | 6.5 | 0.139 | 0.094 | 95.4 | | |
| Example 36 | HT-3 | C-1 | 4.6 | 5.9 | 0.139 | 0.099 | 96.8 | 1.95 | 4.98 |
| Example 37 | HT-3 | C-47 | 4.8 | 5.3 | 0.139 | 0.098 | 97.4 | 2.00 | 5.35 |
| Example 38 | HT-3 | C-8 | 4.3 | 6.9 | 0.139 | 0.096 | 96.6 | 1.93 | 5.51 |
| Example 39 | HT-3 | C-76 | 4.3 | 7.2 | 0.139 | 0.097 | 95.7 | 1.86 | 5.36 |

In Comparative Example 7, efficiency was increased by inserting hole transport layer 2 which can increase the efficiency by efficiently injecting the holes compared to Comparative Example 1.

In Examples 36 to 39, results in which both efficiency and lifespan were improved were obtained compared to Comparative Example 7 by inserting an electron buffer layer to a constitution having hole transport layer 2.

The tendency with regard to the electron buffer layer was similar even when hole transport layer 2 was inserted or the material of hole transport layer 2 was changed.

Comparative Examples 8 to 11 and Examples 40 to 43: Organic Electroluminescent Device Comprising Various Light-Emitting Materials and Comprising or Non-Comprising an Electron Buffer Layer In Comparative Examples 8 to 10, an OLED device was produced in the same manner as in Comparative Example 1, except for varying the host to another derivative.

Comparative Examples 8 to 10

HI-1(40)/HI-2(5)/HT-1(25)/H-x:D-2(20, 2 wt %)/ETL-1: EIL-1(36)/EIL-1(2)/Al(80)

Comparative Example 11

HI-1(40)/HI-2(5)/HT-1(25)/H-1:D-1(20, 2 wt %)/ETL-1: EIL-1(36)/EIL-1(2)/Al(80)

In Example 43, an OLED device was produced in the same manner as in Comparative Example 11, except for shortening the thickness of the electron transport layer to 27 nm, and inserting an electron buffer layer of 9 nm between the light-emitting layer and the electron transport layer.

Example 43

HI-1(40)/HI-2(5)/HT-1(25)/H-1:D-1(20, 2 wt %)/BF-23 (9)/ETL-1:EIL-1(27)/EIL-1(2)/Al(80)

The measured results of the driving voltage, luminous efficiency, CIE color coordinate, and lifespan of Comparative Examples 8 to 11 and Examples 41 to 43 are shown in Table 11.

TABLE 11

| | Host | Dopant | Electron buffer layer | Voltage (V) | Efficiency (cd/A) | Color coordinate (x) | Color coordinate (y) | Lifespan (10 hr) (%) |
|---|---|---|---|---|---|---|---|---|
| Comp. Ex. 8 | H-21 | D-2 | — | 3.9 | 4.1 | 0.140 | 0.090 | 89.9 |
| Comp. Ex. 9 | H-25 | D-2 | — | 4.2 | 4.0 | 0.140 | 0.092 | 94.3 |
| Comp. Ex. 10 | H-2 | D-2 | — | 4.1 | 4.9 | 0.141 | 0.096 | 95.8 |
| Comp. Ex. 11 | H-1 | D-1 | — | 4.1 | 5.8 | 0.147 | 0.124 | 95.8 |
| Example 40 | H-21 | D-2 | C-1 | 4.5 | 3.7 | 0.141 | 0.093 | 91.8 |
| Example 41 | H-25 | D-2 | C-1 | 4.7 | 3.7 | 0.140 | 0.090 | 96.5 |
| Example 42 | H-2 | D-2 | C-1 | 4.6 | 4.5 | 0.141 | 0.098 | 97.6 |
| Example 43 | H-1 | D-1 | C-1 | 4.4 | 5.7 | 0.146 | 0.126 | 98.1 |

In Examples 40 to 42, an OLED device was produced in the same manner as in Comparative Example 8, except for shortening the thickness of the electron transport layer to 27 nm, and inserting an electron buffer layer of 9 nm between the light-emitting layer and the electron transport layer.

Examples 40 to 42

HI-1(40)/HI-2(5)/HT-1(25)/H-x:D-2(20, 2 wt %)/C-1(9)/ ETL-1:EIL-1(27)/EIL-1(2)/Al(80)

In Comparative Example 11, an OLED device was produced in the same manner as in Comparative Example 1, except for changing the blue dopant to compound D-1.

In Examples 40 to 42, hosts other than H-1 were used since C-1 material was used for the electron buffer layer which can improve lifespan compared to Comparative Examples 8 to 10. As a result, similar tendency was shown compared to a device not having any electron buffer layer even for other hosts.

From Comparative Example 11 and Example 43, it is verified that similar tendency is shown in accordance with existence of the electron buffer layer of C-1 even for stilbene dopants such as dopant D-1. As a result, a similar characteristic of a device having an electron buffer layer is proven even for the changes in host and dopant.

| Reference Numbers | | | |
|---|---|---|---|
| 100: | organic electroluminescent device | 101: | substrate |
| 110: | first electrode | 120: | organic layer |
| 122: | hole injection layer | 123: | hole transport layer |
| 125: | light-emitting layer | 126: | electron buffer layer |
| 127: | electron transport layer | 128: | electron injection layer |
| 129: | electron transport zone | 130: | second electrode |

The invention claimed is:

1. An organic electroluminescent device comprising a first electrode; a second electrode facing the first electrode; a light-emitting layer between the first electrode and the second electrode; and an electron transport zone and an electron buffer layer between the light-emitting layer and the second electrode, wherein the light-emitting layer comprises a host and a dopant;

wherein the electron buffer layer comprises a compound comprising a nitrogen-containing heteroaryl selected from the compounds represented by the following formula 1:

H-(Cz-L$_1$)$_a$-M  (1)

wherein
Cz represents the following structure:

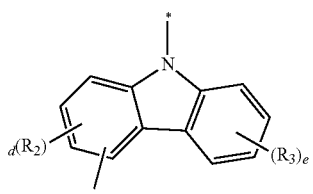

wherein the asterisks (*) denote the point of attachment to H and L$_1$ in formula 1, and N of Cz is attached to L$_1$;
R$_2$ and R$_3$ each independently represent hydrogen, deuterium, a substituted or unsubstituted (C1-C30)alkyl, an unsubstituted (C6-C30)aryl, or —SiR$_6$R$_7$R$_8$;
R$_6$ to R$_8$ each independently represent a substituted or unsubstituted (C1-C30)alkyl, or a substituted or unsubstituted (C6-C30)aryl;
L$_1$ represents a single bond, a substituted or unsubstituted (C6-C30)arylene, or a substituted or unsubstituted (5- to 30-membered)heteroarylene;
M represents a substituted or unsubstituted (5- to 30-membered)heteroaryl;
a represents 1;
d each independently represent an integer of 1 to 3;
e each independently represent an integer of 1 to 4;
where d is an integer of 2 or 3, each of R$_2$ may be the same or different; and
where e is an integer of 2 to 4, each of R$_3$ may be the same or different, and
wherein the LUMO (lowest unoccupied molecular orbital) energy level of the electron buffer layer (Ab) and the LUMO energy level of the host (Ah) have the following equational relationship:

$Ab \leq Ah + 0.5$ eV.

2. The organic electroluminescent device according to claim 1, wherein the electron buffer layer is disposed between the light-emitting layer and the electron transport zone.

3. The organic electroluminescent device according to claim 1, wherein the light-emitting layer comprises an anthracene-derivative fluorescent host, and a pyrene-based fluorescent dopant.

4. The organic electroluminescent device according to claim 1, wherein a hole injection layer and a hole transport layer are comprised between the first electrode and the light-emitting layer.

5. The organic electroluminescent device according to claim 1, wherein the electron transport zone comprises an electron injection layer, and the electron injection layer comprises a metal complex of lithium quinoline.

6. The organic electroluminescent device according to claim 1, wherein the organic electroluminescent device emits blue light.

7. The organic electroluminescent device according to claim 1, wherein the compound comprising a nitrogen-containing heteroaryl is selected from the group consisting of:

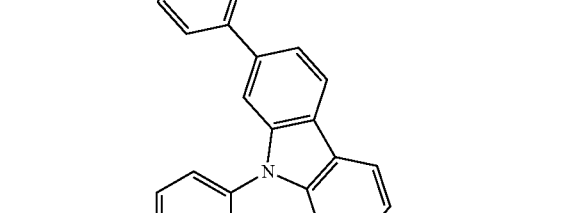
C-6

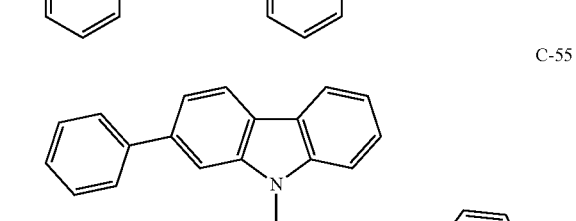
C-55

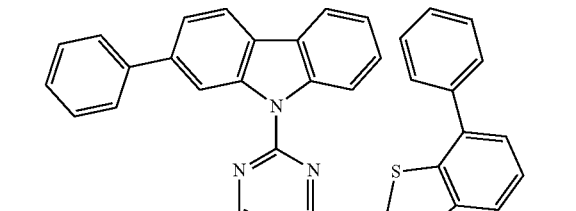
C-65

C-66
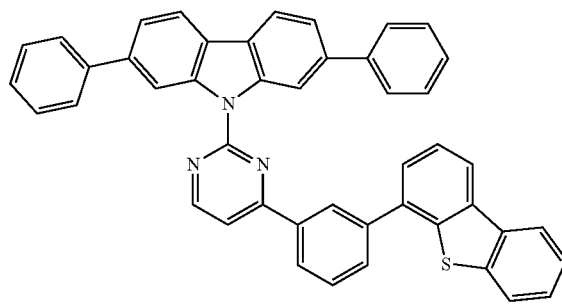
C-68
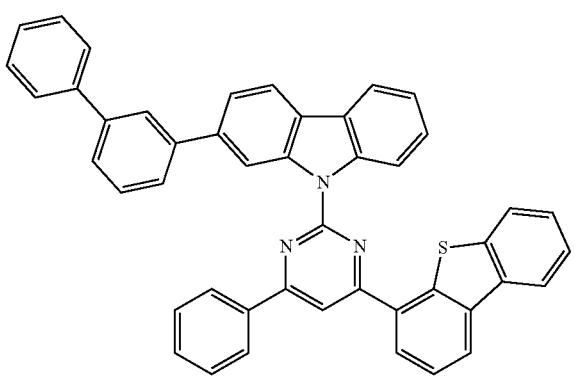
C-70
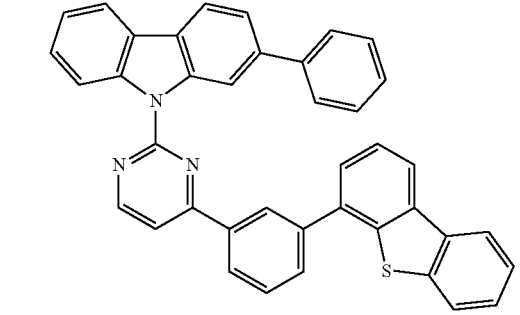
C-71
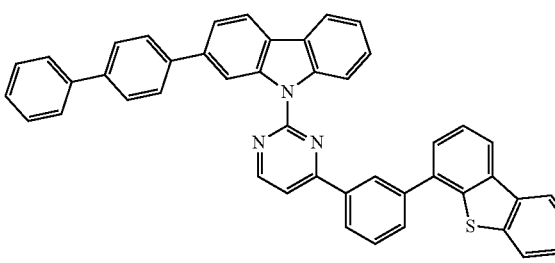
C-72
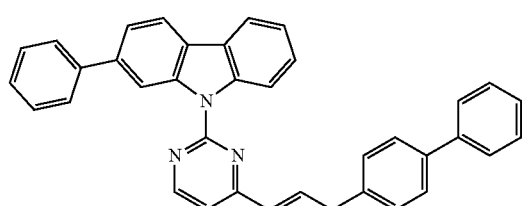
C-73
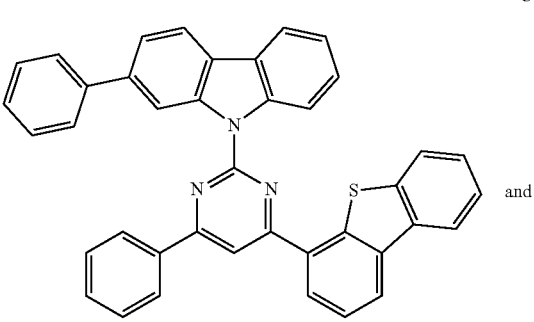
and
C-74
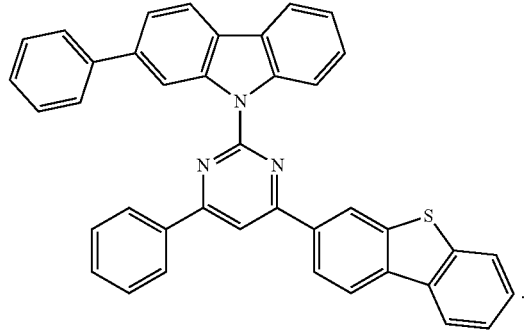
* * * * *

UNITED STATES PATENT AND TRADEMARK OFFICE
CERTIFICATE OF CORRECTION

| | |
|---|---|
| PATENT NO. | : 11,751,476 B2 |
| APPLICATION NO. | : 17/328729 |
| DATED | : September 5, 2023 |
| INVENTOR(S) | : Sang-Hee Cho et al. |

Page 1 of 1

It is certified that error appears in the above-identified patent and that said Letters Patent is hereby corrected as shown below:

In the Claims

Column 83, approx. Line 27-36, the correct structure is:

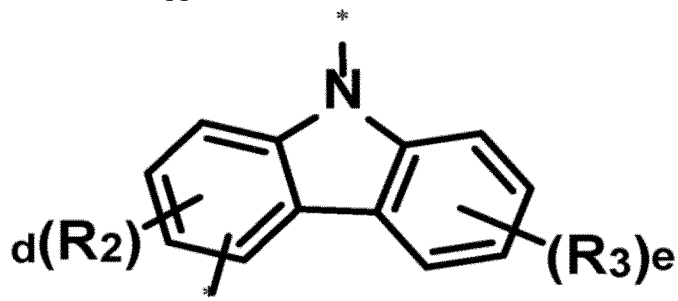

Signed and Sealed this
Twelfth Day of November, 2024

Katherine Kelly Vidal
*Director of the United States Patent and Trademark Office*